United States Patent
Webster-Gardiner et al.

(10) Patent No.: US 12,151,993 B2
(45) Date of Patent: Nov. 26, 2024

(54) SELECTIVE 1-HEXENE/1-OCTENE PRODUCTION WITH 1-DECENE

(71) Applicant: Chevron Phillips Chemical Company LP, The Woodlands, TX (US)

(72) Inventors: Michael S. Webster-Gardiner, Humble, TX (US); Steven M. Bischof, Spring, TX (US); James Hillier, Porter, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 156 days.

(21) Appl. No.: 18/050,510

(22) Filed: Oct. 28, 2022

(65) Prior Publication Data
US 2023/0101033 A1    Mar. 30, 2023

Related U.S. Application Data

(63) Continuation-in-part of application No. 17/471,278, filed on Sep. 10, 2021, now Pat. No. 11,498,889.

(51) Int. Cl.
*C07C 1/207* (2006.01)
*C07C 5/22* (2006.01)
(Continued)

(52) U.S. Cl.
CPC ............ *C07C 1/207* (2013.01); *C07C 5/2206* (2013.01); *C07C 6/04* (2013.01); *C07C 11/107* (2013.01)

(58) Field of Classification Search
CPC ......... C07C 1/207; C07C 5/2206; C07C 6/04; C07C 11/107; C07C 2531/24; C07C 2/08;
(Continued)

(56) References Cited

U.S. PATENT DOCUMENTS

| 4,272,444 A | 6/1981 | McCombs |
| 8,765,984 B2 | 7/2014 | Upshaw |

(Continued)

FOREIGN PATENT DOCUMENTS

| CA | 1048533 A | 2/1979 |
| EP | 1892280 A1 | 2/2008 |

(Continued)

OTHER PUBLICATIONS

International Search Report and Written Opinion issued in corresponding PCT Application No. PCT/US2023/077623, mailed on Feb. 19, 2024, 11 pp.
Capaldo, "Hydrogen Atom Transfer (HAT): A Versatile Strategy forSubstrate Activation in Photocatalyzed Organic Synthesis", Eur. J. Org. Chem. 2017, 2056-2071.
Dietl, "Thermal Hydrogen-Atom Transfer from Methane: The Role of Radicals and Spin States in Oxo-Cluster Chemistry", Angew. Chem. Int. Ed., vol. 51 (23), Jun. 4, 2012, 5544-5555.

(Continued)

*Primary Examiner* — Ali Z Fadhel
(74) *Attorney, Agent, or Firm* — Merchant & Gould P.C.

(57) ABSTRACT

A process to produce 1-octene and 1-decene includes (a) separating a composition containing an oligomer product—which contains 15 to 80 mol % $C_6$ olefins, 20 to 80 mol % $C_8$ olefins, and 5 to 20 mol % $C_{10}+$ olefins—into a first oligomer composition containing $C_6$ alkanes and at least 85 mol % $C_6$ olefins (e.g., 1-hexene), a second oligomer composition containing at least 20 mol % $C_8$ olefins (e.g., 1-octene), and a heavies stream containing $C_{10}+$ olefins, then (b) contacting a metathesis catalyst system with the first oligomer composition to form a first composition comprising $C_{10}$ linear internal olefins, (c) contacting the $C_{10}$ linear internal olefins with a catalytic isomerization catalyst system in the presence of photochemical irradiation to form a second composition comprising 1-decene, and (d) purifying the second composition to isolate a third composition comprising at least 90 mol % 1-decene. Processes to produce 1-hexene and 1-decene also are described, as well as related manufacturing systems and processes to produce higher (Continued)

carbon number normal alpha olefins from lower carbon number normal alpha olefins.

22 Claims, 3 Drawing Sheets

(51) Int. Cl.
*C07C 6/04* (2006.01)
*C07C 11/107* (2006.01)

(58) Field of Classification Search
CPC .. C07C 5/22; C07C 7/00; C07C 45/50; C07C 1/2076; B01J 31/1805; B01J 31/1815; B01J 31/188; B01J 2231/52; B01J 2531/827; B01J 31/2273; B01J 31/2404; B01J 2231/543; B01J 2531/845; B01J 2231/20; B01J 2531/821; B01J 31/2278
See application file for complete search history.

(56) References Cited

U.S. PATENT DOCUMENTS

| | | |
|---|---|---|
| 9,115,069 B2 | 8/2015 | Papp |
| 9,962,689 B2 | 5/2018 | Carney |
| 10,183,899 B2 | 1/2019 | Bischof |
| 10,329,212 B2 | 6/2019 | Fern |
| 10,414,698 B2 | 9/2019 | Fern |
| 10,414,699 B2 | 9/2019 | Bischof |
| 10,435,334 B2 | 10/2019 | Bischof |
| 10,435,336 B2 | 10/2019 | Kreischer |
| 10,464,862 B2 | 11/2019 | Bischof |
| 10,493,422 B2 | 12/2019 | Bischof |
| 10,519,077 B2 | 12/2019 | Kreischer |
| 11,267,909 B2 | 3/2022 | Bischof |
| 11,498,889 B1 | 11/2022 | Bischof |
| 2002/0193650 A1 | 12/2002 | Goze |
| 2004/0054241 A1 | 3/2004 | Maas |
| 2007/0004939 A1 | 1/2007 | Volland |
| 2011/0160495 A1 | 6/2011 | Hasling |
| 2013/0274482 A1 | 10/2013 | Schrock |
| 2018/0127329 A1 | 5/2018 | Bischof |
| 2019/0262819 A1 | 8/2019 | Dong |
| 2019/0263729 A1 | 8/2019 | Bischof |
| 2021/0078920 A1 | 3/2021 | Cruz |

FOREIGN PATENT DOCUMENTS

| | | |
|---|---|---|
| WO | 200100546 W | 1/2001 |
| WO | 200105735 W | 1/2001 |
| WO | 2014088800 A1 | 6/2014 |
| WO | 2015094813 A1 | 6/2015 |
| WO | 2019165350 A1 | 8/2019 |

OTHER PUBLICATIONS

Occhialini, "Catalytic, contra-Thermodynamic Positional Alkene Isomerization", J. Am. Chem. Soc. 2022, 144, 145-152.
Wu, et al. "Tandem Catalysis: Transforming Alcohols to Alkene by Oxidative Dehydroxymethylation." J. Am. Chem. Soc. vol. 140. 2018. pp. 10126-10130.
Xie, et al., "New Catalytic Radical Process Involving 1,4-Hydrogen Atom Abstraction: Asymmetric Construction of Cyclobutanones", J. Am. Chem. Soc. 2021, 143, 30, 11670-11678.
Zhao, et al., "Contra-Thermodynamic Positional Isomerization of Olefins", J. Am. Chem. Soc. 2022, 144, 137-144.
Chatterjee et al., "A General Model for Selectivity in Olefin Cross Metathesis", J. Am. Chem. Soc., 2003, 125, 11360-11370.
Chatterjee et al., "A General Model for Selectivity in Olefin Cross Metathesis", J. Am. Chem. Soc., 2003, Supporting Information, S1-S27.
Haymore et al., "Regioselectivity in Hydroformylation of Linear and Branched Octenes Using HCo(CO)4", Annals NY Academy of Sciences, 1983, 415, 159-175.
Keim, "Oligomerization of Ethylene to alpha-Olefins: Discovery and Development of the Shell Higher Olefin Process (SHOP)", Angew. Chem. Int. Ed., 2013, 52, 12492-12496.
Kreis et al., "A General and Convenient Method for the Rhodium-Catalyzed Decarbonylation of Aldehydes", ChemInform, Wiley-BCH Verlag GMBH&Co, KGAA, DE, 2007, 38, 6.
Landis, "Construction and deconstruction of aldehydes by transfer hydroformylation", Science, 2015, 347, 6217, 29-30.
Malcho et al., "Ionic liquids as recyclable and separable reaction media in Rh-catalyzed decarbonylation of aromatic and aliphatic aldehydes", RSC Adv, 2014, 4, 102, 58151-58155.
Murphy, "Rh-catalyzed C—C bond cleavage by transfer hydroformylation", Science, 2015, 347, 56, 6217, 55-60.
Murphy, "Rh-catalyzed C—C bond cleavage by transfer hydroformylation", Science, 2015, 347, 6217, Supporting Information, S1-S70.
Olsen et al., "Iridium-Catalyzed Dehydrogenative Decarbonylation of Primary Alcohols with the Liberation of Syngas", Chem. Eur. J., 2012, 18, 50, 16023-16029.
Pandey et al., "Terminal Olefins, from Aldehydes through Enol Triflate Reduction", J. Org. Chem., 2007, 72, 7769-7770.
Selent et al., "New Phosphorus Ligands for the Rhodium-Catalyzed Isomerization/Hydroformylation of Internal Octenes", Angew. Chem. Int. Ed., 2001, 40, 9, 1696-1698.
Thomas et al., "Highly Selective Ruthenium Metathesis Catalysts for Ethenolysis", J. Am. Chem. Soc., 2011, 133, 7490-7496.
Thomas et al., "Highly Selective Ruthenium Metathesis Catalysts for Ethenolysis", J. Am. Chem. Soc., 2011, Supporting Information, S1-S32.
Tsuji et al., "Organic Synthesis by Means of Noble Metal Compounds. XXXV. Novel Decarbonylation Reactions of Aldehydes and Acyl Halides Using Rhodium Complexes", Journal of the American Chemical Society, 1968, 90, 1, 99-107.

SELECTIVE 1-HEXENE/1-OCTENE PRODUCTION WITH 1-DECENE

REFERENCE TO RELATED APPLICATION

This application is a continuation-in-part application of co-pending U.S. patent application Ser. No. 17/471,278, filed on Sep. 10, 2021, now U.S. Pat. No. 11,498,889, the disclosure of which is incorporated herein by reference in its entirety.

FIELD OF THE INVENTION

The present disclosure relates generally to systems and methods for producing 1-decene in combination with 1-hexene, 1-octene, or both 1-hexene and 1-octene.

BACKGROUND OF THE INVENTION

The synthesis of specific carbon number normal alpha olefins—in particular, 1-hexene, 1-octene, and 1-decene—are of significant importance in the chemical industry. However, with current catalysts and reaction processes, it is difficult to selectively produce only the desired carbon number alpha olefin fraction, rather than a complex mixture of olefin products. It would be beneficial to develop new ways to produce desirable combinations of specific $C_6$-$C_{10}$ alpha olefins. Accordingly, it is to these ends that the present invention is generally directed.

SUMMARY OF THE INVENTION

This summary is provided to introduce a selection of concepts in a simplified form that are further described herein. This summary is not intended to identify required or essential features of the claimed subject matter. Nor is this summary intended to be used to limit the scope of the claimed subject matter. A first process described herein can be used to produce 1-octene and 1-decene. This first process can comprise a) separating a composition comprising an oligomer product, the oligomer product comprising from 15 to 80 mol % $C_6$ olefins, from 20 to 80 mol % $C_8$ olefins, and from 5 to 20 mol % $C_{10}+$ olefins, into i) a first oligomer composition comprising $C_6$ alkanes and at least 85 mol % $C_6$ olefins, the $C_6$ olefins comprising at least 80 mol % 1-hexene, ii) a second oligomer composition comprising at least 20 mol % $C_8$ olefins, the $C_8$ olefins comprising at least 85 mol % 1-octene, and iii) a heavies stream comprising $C_{10}+$ olefins, b) contacting a metathesis catalyst system with all or a portion of the first oligomer composition to form a first composition comprising $C_{10}$ linear internal olefins, c) contacting all or a portion of the $C_{10}$ linear internal olefins with a catalytic isomerization catalyst system in the presence of photochemical irradiation to form a second composition comprising 1-decene, and d) purifying the second composition to isolate a third composition comprising at least 90 mol % 1-decene.

A second process described herein can be used to produce 1-hexene and 1-decene. This second process can comprise a) separating a composition comprising an oligomer product, the oligomer product comprising at least 85 mol % $C_6$ olefins and at least 5 mol % $C_8+$ olefins, into i) a first oligomer composition comprising $C_6$ alkanes and at least 90 mol % $C_6$ olefins, the $C_6$ olefins comprising at least 90 mol % 1-hexene, and ii) a heavies stream comprising $C_8+$ olefins, b) contacting a metathesis catalyst system with all or a portion of the first oligomer composition to form a first composition comprising $C_{10}$ linear internal olefins, c) contacting all or a portion of the $C_{10}$ linear internal olefins with a catalytic isomerization catalyst system in the presence of photochemical irradiation to form a second composition comprising 1-decene, and d) purifying the second composition to isolate a third composition comprising at least 90 mol % 1-decene.

Related manufacturing systems also are disclosed herein. A first (1-octene and 1-decene) manufacturing system can comprise 1) an ethylene oligomerization system configured to oligomerize ethylene in the presence of a catalyst system or catalyst system components to form a composition comprising an oligomer product, the oligomer product comprising from 15 to 80 mol % $C_6$ olefins, from 20 to 80 mol % $C_8$ olefins, and from 5 to 20 mol % $C_{10}+$ olefins, 2) a fractionation system configured to separate the composition comprising the oligomer product into i) a first oligomer composition comprising 1-hexene, ii) a second oligomer composition comprising 1-octene, and iii) a heavies stream comprising $C_{10}+$ olefins, 3) a metathesis system configured to contact a metathesis catalyst system with all or a portion of the first oligomer composition to form a first composition comprising $C_{10}$ linear internal olefins, 4) a catalytic isomerization system configured to contact all or a portion of the $C_{10}$ linear internal olefins with a catalytic isomerization catalyst system in the presence of photochemical irradiation to form a second composition comprising 1-decene, and 5) a purification system configured to isolate a third composition comprising at least 90 mol % 1-decene from the second composition.

A second (1-hexene and 1-decene) manufacturing system can comprise 1) an ethylene oligomerization system configured to oligomerize ethylene in the presence of a catalyst system or catalyst system components to form a composition comprising an oligomer product, the oligomer product comprising at least 85 mol % $C_6$ olefins and at least 5 mol % $C_8+$ olefins, 2) a fractionation system configured to separate the composition comprising the oligomer product into a first oligomer composition comprising 1-hexene and a heavies stream comprising $C_8+$ olefins, 3) a metathesis system configured to contact a metathesis catalyst system with all or a portion of the first oligomer composition to form a first composition comprising $C_{10}$ linear internal olefins, 4) a catalytic isomerization system configured to contact all or a portion of the $C_{10}$ linear internal olefins with a catalytic isomerization catalyst system in the presence of photochemical irradiation to form a second composition comprising 1-decene, and 5) a purification system configured to isolate a third composition comprising at least 90 mol % 1-decene from the second composition.

A third process described herein can be used to produce a higher carbon number normal alpha olefin from a lower carbon number normal alpha olefin. This process can comprise (i) contacting a first normal alpha olefin having the structure $CH_3(CH_2)_nHC=CH_2$ and a metathesis catalyst system to form a linear internal olefin having the structure $CH_3(CH_2)_nHC=CH(CH_2)_nCH_3$, and (ii) contacting the linear internal olefin with a catalytic isomerization catalyst system in the presence of photochemical irradiation to form a second normal alpha olefin having the structure $CH_3(CH_2)_{n+1}HC=CH_2$. In the third process, n is an integer that can range from 0 to 15.

A fourth process described herein can be used to produce a higher carbon number normal alpha olefin from two lower carbon number normal alpha olefins. This process can comprise (a) contacting a first normal alpha olefin having the structure $CH_3(CH_2)_pHC=CH_2$ and a second normal alpha olefin having the structure $CH_3(CH_2)_qHC=CH_2$ and a metathesis catalyst system to form a linear internal olefin having the structure $CH_3(CH_2)_pHC=CH(CH_2)_qCH_3$, and (b) contacting the linear internal olefin with a catalytic isomerization catalyst system in the presence of photochemical irradiation to form a third normal alpha olefin having the structure $CH_3(CH_2)_{p+q+1}HC=CH_2$. In the fourth process, p and q independently are integers in a range from 0 to 15. While p and q can be the same integer, typically p and q are different integers.

Both the foregoing summary and the following detailed description provide examples and are explanatory only. Accordingly, the foregoing summary and the following detailed description should not be considered to be restrictive. Further, features or variations can be provided in addition to those set forth herein. For example, certain aspects can be directed to various feature combinations and sub-combinations described in the detailed description.

BRIEF DESCRIPTION OF THE FIGURES

The following figures form part of the present specification and are included to further demonstrate certain aspects of the present invention. The invention may be better understood by reference to one or more of these figures in combination with the detailed description.

Figure 1:
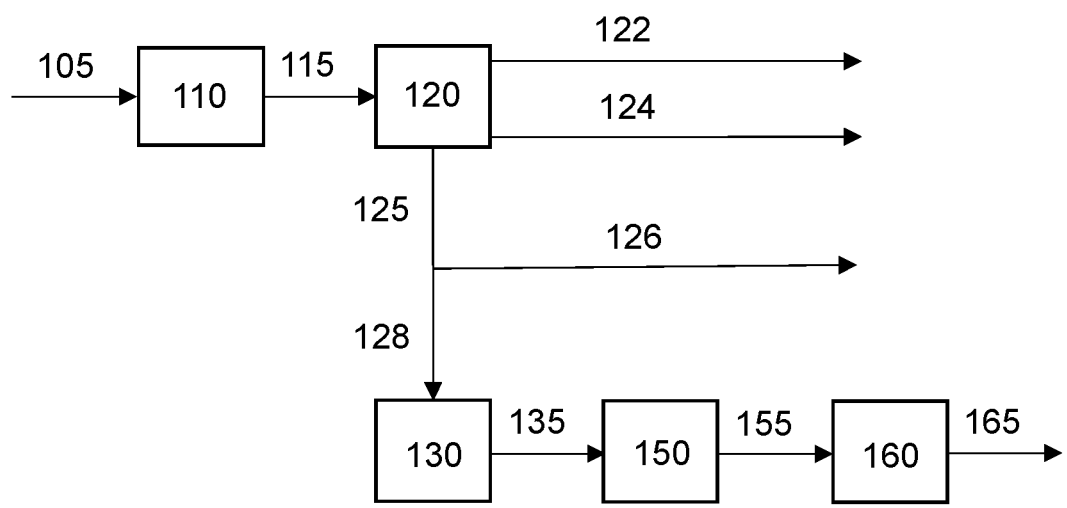
FIG. 1 illustrates a 1-octene/1-decene manufacturing system consistent with an aspect of the present disclosure.

While the inventions disclosed herein are susceptible to various modifications and alternative forms, only a few specific aspects have been shown by way of example in the drawings and described in detail below. The figures and detailed descriptions of these specific aspects are not intended to limit the breadth or scope of the inventive concepts or the appended claims in any manner. Rather, the figures and detailed descriptions are provided to illustrate the inventive concepts to a person of ordinary skill in the art and to enable such person to make and use the inventive concepts.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter can be described such that, within particular aspects, a combination of different features can be envisioned. For each and every aspect and/or feature disclosed herein, all combinations that do not detrimentally affect the designs, compositions, processes, and/or methods described herein are contemplated with or without explicit description of the particular combination. Additionally, unless explicitly recited otherwise, any aspect and/or feature disclosed herein can be combined to describe inventive features consistent with the present disclosure.

In this disclosure, while compositions, processes/methods, and systems are described in terms of "comprising" various materials, steps, and components, the compositions, processes/methods, and systems also can "consist essentially of" or "consist of" the various materials, steps, or components, unless stated otherwise.

The terms "a," "an," and "the" are intended to include plural alternatives, e.g., at least one, unless otherwise specified. For instance, the disclosure of "a $C_8$ olefin" or "a Bronsted base" is meant to encompass one, or combinations of more than one, $C_8$ olefin or Bronsted base, respectively, unless otherwise specified.

Generally, groups of elements are indicated using the numbering scheme indicated in the version of the periodic table of elements published in *Chemical and Engineering News,* 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to hexene (or hexenes) includes all linear or branched, acyclic or cyclic, hydrocarbon compounds having six carbon atoms and 1 carbon-carbon double bond; a general reference to pentane includes n-pentane, 2-methyl-butane, and 2,2-dimethylpropane; and a general reference to a butyl group includes an n-butyl group, a sec-butyl group, an iso-butyl group, and a t-butyl group.

The terms "contacting" and "combining" are used herein to describe compositions, processes/methods, and systems in which the materials are contacted or combined together in any order, in any manner, and for any length of time, unless otherwise specified. For example, the materials can be blended, mixed, slurried, dissolved, reacted, treated, impregnated, compounded, or otherwise contacted or combined in some other manner or by any suitable method or technique.

The terms "catalyst composition," "catalyst mixture," "catalyst system," and the like, do not depend upon the actual product or composition resulting from the contact or reaction of the initial components of the disclosed or claimed catalyst composition/mixture/system, the nature of the active catalytic site, or the fate of the initial components after the components have been combined. Therefore, the terms "catalyst composition," "catalyst mixture," "catalyst system," and the like, encompass the initial starting components of the composition, as well as whatever product(s) may result from contacting these initial starting components, and this is inclusive of both heterogeneous and homogenous catalyst systems or compositions. The terms "catalyst composition," "catalyst mixture," "catalyst system," and the like, can be used interchangeably throughout this disclosure.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g., halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl groups are derived by removal of a hydrogen atom from a primary, secondary, or tertiary carbon atom, respectively, of an alkane. The n-alkyl group can be derived by removal of a hydrogen atom from a terminal carbon atom of a linear alkane.

The term "olefin" whenever used in this specification and claims refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s).

The term "alpha olefin" as used herein refers to any olefin that has a carbon-carbon double bond between the first and second carbon atom of the longest contiguous chain of carbon atoms. The term "alpha olefin" includes linear and branched alpha olefins and alpha olefins which can have more than one non-aromatic carbon-carbon double bond, unless expressly stated otherwise. The term "normal alpha olefin" as used herein refers to a linear aliphatic hydrocarbon mono-olefin having a carbon-carbon double bond between the first and second carbon atoms. The term "linear internal olefin" as used herein refers to a linear aliphatic hydrocarbon mono-olefin having a double bond that is not between the first and second carbon atoms.

An "aromatic compound" refers to a compound containing a cyclically conjugated moiety that follows the Hückel (4n+2) rule and containing (4n+2) pi-electrons, where n is an integer from 1 to about 5. Aromatic compounds can be monocyclic or polycyclic, unless otherwise specified. Non-limiting examples of aromatic compounds include benzene, naphthalene, and toluene, among others.

The term "substituted" when used to describe a compound or group, for example, when referring to a substituted analog of a particular compound or group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents, unless otherwise specified.

The term oligomer refers to a product that contains from 2 to 20 monomer units. The terms "oligomerization product" and "oligomer product" include all products made by the "oligomerization" process, including the "oligomers" and products which are not "oligomers" (e.g., products which contain more than 20 monomer units, or solid polymer), but exclude other non-oligomer components of an oligomerization reaction zone effluent stream, such as unreacted ethylene, organic reaction medium, and hydrogen, amongst other components.

The term "oligomerization" and its derivatives refer to processes which produce an oligomer product comprising at least 20 wt. %, 35 wt. %, 50 wt. %, or 60 wt. % products comprising from 2 to 20 monomer units. In an example, an "oligomerization" process using ethylene as the monomer produces a mixture of products comprising at least 20 wt. %, 35 wt. %, 50 wt. %, or 60 wt. % oligomers having from 4 to 40 carbon atoms.

The term "reaction zone effluent" and it derivatives (e.g., oligomerization reaction zone effluent) generally refer to all the material which exits the reaction zone through a reaction zone outlet/discharge which discharges a reaction mixture and can include reaction zone feed(s) (e.g., ethylene, catalyst system or catalyst system components, and/or solvent), and/or reaction product (e.g., oligomer product including oligomers and non-oligomers). The term "reaction zone effluent" and its derivatives can be qualified to refer to certain portions by use of additional qualifying terms. For example, while reaction zone effluent refers to all material which exits the reaction zone through the reaction zone outlet/discharge, a reaction zone oligomer product effluent refers to only the oligomer product within the reaction zone effluent.

As utilized herein, the term "solvent" applies to a material which can dissolve a compound, or a material which can dilute the components of a reaction. As such, the term "solvent" can encompass materials which can act as a diluent, unless stated otherwise.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, when a chemical moiety having a certain number of carbon atoms is disclosed or claimed, the intent is to disclose or claim individually every possible number that such a range could encompass, consistent with the disclosure herein. For example, the disclosure that a moiety is a $C_1$ to $C_{18}$ hydrocarbyl group, or in alternative language, a hydrocarbyl group having from 1 to 18 carbon atoms, as used herein, refers to a moiety that can have 1, 2, 3, 4, 5, 6, 7, 8, 9, 10, 11, 12, 13, 14, 15, 16, 17, or 18 carbon atoms, as well as any range between these two numbers (for example, a $C_1$ to $C_8$ hydrocarbyl group), and also including any combination of ranges between these two numbers (for example, a $C_2$ to $C_4$ and a $C_{12}$ to $C_{16}$ hydrocarbyl group). Likewise, all other ranges disclosed herein should be interpreted in a manner similar to this example.

In general, an amount, size, formulation, parameter, range, or other quantity or characteristic is "about" or "approximate" whether or not expressly stated to be such. Whether or not modified by the term "about" or "approximately," the claims include equivalents to the quantities or characteristics.

Features within this disclosure that are provided as minimum values can be alternatively stated as "at least" or "greater than or equal to" any recited minimum value for the feature disclosed herein. Features within this disclosure that are provided as maximum values can be alternatively stated as "less than or equal to" or "below" any recited maximum value for the feature disclosed herein.

Although any methods and materials similar or equivalent to those described herein can be used in the practice or testing of the invention, the typical methods and materials are herein described.

All publications and patents mentioned herein are incorporated herein by reference in their entirety for the purpose of describing and disclosing, for example, the constructs and methodologies that are described in the publications and patents, which might be used in connection with the presently described invention.

DETAILED DESCRIPTION OF THE INVENTION

Disclosed herein are systems and processes for producing 1-decene in combination with 1-hexene, 1-octene, or both 1-hexene and 1-octene, as well as general processes for producing a higher carbon number normal alpha olefin from a lower carbon number normal alpha olefin.

The development of processes to selectively synthesize 1-decene is uniquely challenging. The ethylene oligomerization processes that are used to generate 1-hexene and 1-octene often involve a metallocycle mechanism, which does not operate effectively for higher oligomers, such as 1-decene and above. While not wishing to be bound by theory, it is believed that intermediate chromacycles are not stable and readily fall apart before allowing insertion of the 5th ethylene to generate a 11-membered ring. Therefore, 1-decene is typically synthesized through chemical reactions and using catalyst systems that are not selective for one specific molecule (1-decene), but rather produce an array of materials that must be inefficiently separated or fractionated. The ethylene efficiency of a process to produce 1-decene would be very low, given all the other product fractions that are simultaneously being produced.

A first objective of the present invention is a system and process for producing 1-octene and 1-decene, in which an ethylene oligomerization product stream containing 1-hexene and 1-octene is separated, with the 1-octene portion being a primary product, while the 1-hexene portion is typically of lower purity (e.g., less than 95 mol %, based on $C_6$). Further, the $C_6$ fraction containing 1-hexene also contains internal and cyclic $C_6$ materials that are difficult to separate without large and complicated distillation columns and processes. Instead of purifying and cleaning up the impure $C_6$ stream, it is subjected herein to metathesis and catalytic isomerization, ultimately converting most of the 1-hexene into 1-decene, thus resulting in a selective octene/decene process. Alternatively, an on-purpose 1-hexene system can be used to supply the 1-hexene for metathesis and subsequent catalytic isomerization.

For instance, many end-uses for 1-hexene require purities of 99 mol % or more (based on $C_6$), but as shown in the Table I for an illustrative $C_6$ fraction from an ethylene oligomerization process, it is not uncommon for the purity of 1-hexene to be ~90 mol %, and the other $C_6$ species present having boiling points within 5-15° C. of 1-hexene. From Table I, it is apparent that the boiling points of the $C_6$ species are very close, leading to complicated separations with large distillation columns in order to isolate 1-hexene at over 99 mol % purity. Beneficially, subjecting the species in Table I to metathesis would result in a far easier separation process, since only 1-hexene would metathesize to 5-decene, and the alkane impurities (e.g., $C_6$ alkanes generally do not metathesize) or metathesized olefin impurities (which would not result in decene) would be significantly easier to separate from 5-decene than to separate them as the $C_6$ components that are shown in Table I.

TABLE I

| $C_6$ Species | mol % | Boiling Point (° C.) |
|---|---|---|
| 1-hexene | 90.6 | 63 |
| 3-hexene | 0.2 | 66 |
| 2-hexene | 0.1 | 67 |
| n-hexane | 1.1 | 69 |
| methylcyclopentane | 4.4 | 72 |
| methylenecyclopentane | 3.7 | 76 |

Moreover, as opposed to the end-uses for 1-hexene that require purities of 99 mol % or more, most end-use applications for 1-decene only require purities of in the 95-98 mol % range (e.g., 96.5 mol % purity). This further simplifies the purification process for $C_{10}$ hydrocarbons as compared to $C_6$ hydrocarbons, due to the lower purity requirement of the desirable normal alpha olefin.

A second objective of the present invention is a system and process for producing 1-hexene and 1-decene, in which a selective ethylene oligomerization product stream containing 1-hexene is first produced. A portion of the 1-hexene stream is then subjected herein to metathesis and catalytic isomerization, ultimately converting that portion of the 1-hexene into 1-decene, thus resulting in a selective hexene/decene process. A benefit of this hexene/decene system and process is that 1-hexene can be produced continuously, while 1-decene can be produced on demand or as-needed.

These disclosed systems and processes provide the simultaneous production of 1-decene and 1-hexene, or 1-decene and 1-octene. Advantageously, the relative amount of 1-decene produced in these systems and processes can be varied based on market demands, production capacity, and profit margins of the respective normal alpha olefin (e.g., 1-decene versus 1-hexene).

A third objective of the present invention is a process for producing a higher carbon number normal alpha olefin from a lower carbon number normal alpha olefin, in which the lower carbon number normal alpha olefin is subjected to metathesis then catalytic isomerization to produce the higher carbon number alpha olefin. Beneficially, the lower carbon number normal alpha olefin can be 1-butene, and the higher carbon number normal alpha olefin can be 1-hexene, or for instance, the lower carbon number alpha olefin can be 1-pentene (or 1-hexene, or 1-octene), and the higher carbon number normal alpha olefin can be 1-octene (or 1-decene, or 1-tetradecene).

Processes to Make Octene/Decene or Hexene/Decene

Aspects of this invention are directed to processes for producing 1-decene in combination with 1-octene or 1-hexene. A first process described herein can be used to produce 1-octene and 1-decene, and the first process can comprise (or consist essentially of, or consist of) a) separating a composition comprising an oligomer product, the oligomer product comprising from 15 to 80 mol % $C_6$ olefins, from 20 to 80 mol % $C_8$ olefins, and from 5 to 20 mol % $C_{10}+$ olefins, into i) a first oligomer composition comprising $C_6$ alkanes and at least 85 mol % $C_6$ olefins, the $C_6$ olefins comprising at least 80 mol % 1-hexene, ii) a second oligomer composition comprising at least 20 mol % $C_8$ olefins, the $C_8$ olefins comprising at least 85 mol % 1-octene, and iii) a heavies stream comprising $C_{10}+$ olefins, b) contacting a metathesis catalyst system with all or a portion of the first oligomer composition to form a first composition comprising $C_{10}$ linear internal olefins, c) contacting all or a portion of the $C_{10}$ linear internal olefins with a catalytic isomerization catalyst system in the presence of photochemical irradiation to form a second composition comprising 1-decene, and d) purifying the second composition to isolate a third composition comprising at least 90 mol % 1-decene.

A second process described herein can be used to produce 1-hexene and 1-decene, and the second process can comprise (or consist essentially of, or consist of) a) separating a composition comprising an oligomer product, the oligomer product comprising at least 85 mol % $C_6$ olefins and at least 5 mol % $C_8+$ olefins, into i) a first oligomer composition comprising $C_6$ alkanes and at least 90 mol % $C_6$ olefins, the $C_6$ olefins comprising at least 90 mol % 1-hexene, and ii) a heavies stream comprising $C_8+$ olefins, b) contacting a metathesis catalyst system with all or a portion of the first oligomer composition to form a first composition comprising $C_{10}$ linear internal olefins, c) contacting all or a portion of the $C_{10}$ linear internal olefins with a catalytic isomerization catalyst system in the presence of photochemical irradiation to form a second composition comprising 1-decene, and d) purifying the second composition to isolate a third composition comprising at least 90 mol % 1-decene.

Generally, the features of the first process and the second process (e.g., the oligomer product, the first oligomer composition, the second oligomer composition, the metathesis step, the catalytic isomerization step, and the purification step, among other features) are independently described herein and these features can be combined in any combination to further describe these two processes. Moreover, additional process steps can be performed before, during, and/or after the steps of these processes, unless stated otherwise.

Referring now to the first process, step a) separates (or fractionates) a composition comprising an oligomer product—the oligomer product comprising from 15 to 80 mol % $C_6$ olefins, from 20 to 80 mol % $C_8$ olefins, and from 5 to 20 mol % $C_{10}+$ olefins—into i) a first oligomer composition comprising $C_6$ alkanes and at least 85 mol % $C_6$ olefins, the $C_6$ olefins comprising at least 80 mol % 1-hexene, ii) a second oligomer composition comprising at least 20 mol % $C_8$ olefins, the $C_8$ olefins comprising at least 85 mol % 1-octene, and iii) a heavies stream comprising $C_{10}+$ olefins. In step a) of the first process, the composition containing the oligomer product can be a reaction zone effluent from an ethylene oligomerization reactor/system, and can be formed by contacting ethylene, a catalyst system or catalyst system components, optionally an organic reaction medium, and optionally hydrogen in a reaction zone. In an aspect, the catalyst system or the catalyst system components can comprise a heteroatomic ligand chromium compound complex and an alkylaluminum compound, or a heteroatomic ligand, a chromium compound, and an alkylaluminum compound. Hence, in addition to the oligomer product, the composition (e.g., a reaction zone effluent) can contain catalyst (activated or deactivated) and an organic reaction medium. The separating (or fractionating) of the composition containing the oligomer product can occur in one or more steps—usually, multiple steps—to form the first oligomer composition, the second oligomer composition, and the heavies stream. Representative patent documents directed to ethylene oligomerization processes and catalyst systems include U.S. Pat. Nos. 9,962,689, 10,329,212, 10,414,698, 10,414,699, 10,435,336, 10,464,862, 10,493,422, 10,519,077, and 11,267,909.

As it pertains to the first process, the oligomer product in step a) contains 15 to 80 mol % $C_6$ olefins, 20 to 80 mol % $C_8$ olefins, and 5 to 20 mol % $C_{10}+$ olefins prior to separating (or fractionating). For instance, the oligomer product can contain from 25 to 75 mol % $C_6$ olefins in one aspect, from 30 to 70 mol % $C_6$ olefins in another aspect, from 35 to 65 mol % $C_6$ olefins in yet another aspect, and from 40 to 60 mol % $C_6$ olefins in still another aspect. Additionally or alternatively, the oligomer product can contain from 25 to 75 mol % $C_8$ olefins in one aspect, from 30 to 70 mol % $C_8$ olefins in another aspect, from 35 to 65 mol % $C_8$ olefins in yet another aspect, and from 40 to 60 mol % $C_8$ olefins in still another aspect. Additionally or alternatively, the oligomer product can contain from 5 to 18 mol % $C_{10}+$ olefins; alternatively, from 5 to 15 mol % $C_{10}+$ olefins; alternatively, from 7 to 20 mol % $C_{10}+$ olefins; or alternatively, from 7 to 18 mol % $C_{10}+$ olefins. As one of skill in the art would readily recognize, the total of these and other components does not exceed 100 mol %.

The composition containing the oligomer product is separated into i) a first oligomer composition comprising $C_6$ alkanes and at least 85 mol % $C_6$ olefins, the $C_6$ olefins comprising at least 80 mol % 1-hexene, ii) a second oligomer composition comprising at least 20 mol % $C_8$ olefins, the $C_8$ olefins comprising at least 85 mol % 1-octene, and iii) a heavies stream comprising $C_{10}+$ olefins. Referring now to the first oligomer composition which, in some aspects, can contain at least 85 mol %, at least 90 mol %, at least 93 mol %, or at least 95 mol % $C_6$ olefins. Therefore, typical ranges for the amount of $C_6$ olefins in the first oligomer composition can include, but are not limited to, from 85 to 99 mol %, from 90 to 99.5 mol %, from 93 to 98 mol %, from 95 to 99 mol %, and the like. At least 80 mol % of the $C_6$ olefins is 1-hexene, but more often, the $C_6$ olefins contain at least 85 mol %, at least 90 mol %, or at least 95 mol % 1-hexene; therefore, typical ranges include from 80 mol % to 98 mol %, from 80 mol % to 95 mol %, from 85 mol % to 95 mol %, or from 90 to 99 mol % 1-hexene. In addition to 1-hexene, the $C_6$ olefins can contain internal and cyclic $C_6$ olefins (e.g., 2-hexene, 3-hexene, methylenecyclopentane, etc.), and the $C_6$ olefins often can contain from 0.1 to 10 mol %, from 0.5 to 8 mol %, from 0.5 to 6 mol %, from 1 to 8 mol %, or from 1 to 6 mol % of a total of internal and cyclic $C_6$ olefins. $C_6$ alkanes also are present in the first oligomer composition; representative $C_6$ alkanes include methylcyclopentane and n-hexane. Generally, the first oligomer composition contains from 0.5 to 12 mol %, from 0.5 to 10 mol %, from 1 to 10 mol %, from 1 to 8 mol %, from 1.5 to 8 mol %, from 2 to 8 mol %, or from 2 to 6 mol %, $C_6$ alkanes.

In the first process, the second oligomer composition can comprise at least 20 mol % $C_8$ olefins, and the $C_8$ olefins can contain at least 85 mol % 1-octene. In some aspects, the second oligomer composition can contain at least 50 mol %, at least 75 mol %, at least 90 mol %, at least 95 mol %, at least 96 mol %, or at least 97 mol % $C_8$ olefins. Therefore, typical ranges for the amount of $C_8$ olefins in the second oligomer composition can include, but are not limited to, from 20 to 99 mol %, from 50 to 99 mol %, from 75 to 99 mol %, from 85 to 99 mol %, from 90 to 99.5 mol %, from 95 to 99.5 mol %, from 97 to 99 mol %, and the like. At least 85 mol % of the $C_8$ olefins is 1-octene, but more often, the $C_8$ olefins contain at least 90 mol %, at least 95 mol %, or at least 97 mol % 1-octene; therefore, typical ranges include from 85 mol % to 98 mol %, from 90 mol % to 99 mol %, from 95 mol % to 98 mol %, or 97 to 99.5 mol % 1-octene.

Referring now to step b) of the first process, a metathesis catalyst system is contacted with all or a portion of the first oligomer composition to form a first composition comprising $C_{10}$ linear internal olefins. The first composition typically can comprise at least 85 mol %, at least 90 mol %, at least 92 mol %, or at least 95 mol % $C_{10}$ linear internal olefins, based on $C_6$+ olefins in the first oligomer composition. Suitable metathesis catalyst systems for step b) are disclosed hereinbelow, and any suitable conditions for the metathesis step b) can be employed, as would be recognized by those skilled in the art in view of this disclosure, and for example, U.S. Pat. No. 8,765,984.

Optionally, prior to step c), the first process can further comprise a step of isolating a composition comprising at least 90 mol %, at least 93 mol %, or at least 96 mol % $C_{10}$ linear internal olefins from the first composition. Any suitable technique can be used, such as extraction, filtration, evaporation, distillation, and the like, as well as any combination thereof. Beneficially, $C_6$ alkanes in the first oligomer composition do not metathesize, so these materials will be relatively easy to separate from $C_{10}$ linear internal olefins. Likewise, methylenecyclopentane is unreactive in metathesis, so this material also will be relatively easy to separate from $C_{10}$ linear internal olefins. Further, internal $C_6$ olefins metathesize to form non-$C_{10}$ olefins, which also become easier to separate from $C_{10}$ linear internal olefins.

In step c), all or a portion of the $C_{10}$ linear internal olefins (e.g., 5-decene) are contacted with a catalytic isomerization catalyst system in the presence of photochemical irradiation to form a second composition comprising 1-decene. Any suitable catalytic isomerization catalyst system can be used, provided that it is suitable for chain-walking the double bond to the terminal position. Suitable catalytic isomerization catalyst systems for step c) are disclosed hereinbelow, and any suitable conditions for the catalytic isomerization step c) can be employed, as would be recognized by those skilled in the art in view of this disclosure, and for example, J. Am. Chem. Soc. 2022, 144, 137-144; J. Am. Chem. Soc. 2022, 144, 145-152; J. Am. Chem. Soc. 2021, 143, 30, 11670-11678; Eur. J. Org. Chem. 2017, 2056-2071; and Angewandte Chemie International Edition, Volume 51 (23), Jun. 4, 2012.

Generally, a molar yield of 1-decene in step c) can be at least 20%, at least 30%, at least 40%, at least 50%, at least 75%, or at least 90%. This molar yield of 1-decene is based on the initial amount of the $C_{10}$ linear internal olefins that are contacted with the catalytic isomerization catalyst system in the presence of photochemical irradiation in step c).

In step d) of the first process, the second composition—comprising 1-decene—can be purified to isolate a third composition containing at least 90 mol % 1-decene. The third composition containing 1-decene can be isolated or separated from the second composition using any suitable technique, such as extraction, filtration, evaporation, distillation, or any combination of two or more of these techniques. While the third composition contains at least 90 mol % 1-decene, in some aspects, the third composition can contain at least 92 mol %, at least 95 mol %, at least 97 mol %, or at least 98 mol % 1-decene. Therefore, typical ranges for the amount of 1-decene in the third composition can include, but are not limited to, from 90 to 99 mol %, from 92 to 99.5 mol %, from 95 to 99 mol %, from 98 to 99.5 mol %, and the like.

Optionally, the first process can further comprise a step of contacting the metathesis catalyst system with all or a portion of the $C_8$ olefin composition (the second oligomer composition comprising $C_8$ olefins) to form a $C_{14}$ olefin composition. Also optionally, the first process can further comprise a step of contacting the metathesis catalyst with a light oligomer composition comprising $C_6$ and $C_8$ olefins to form a composition comprising $C_{10}$-$C_{14}$ linear internal olefins. The light oligomer composition can be formed by combining, in any relative amounts, at least a portion of the first oligomer composition (containing 1-hexene) and the second oligomer composition (containing 1-octene).

Referring now to the second process, step a) separates (or fractionates) a composition comprising an oligomer product—the oligomer product comprising at least 85 mol % $C_6$ olefins and at least 5 mol % $C_8$+ olefins—into i) a first oligomer composition comprising $C_6$ alkanes and at least 90 mol % $C_6$ olefins, the $C_6$ olefins comprising at least 90 mol % 1-hexene, and ii) a heavies stream comprising $C_8$+ olefins. As with the first process, in step a) of the second process, the composition containing the oligomer product can be a reaction zone effluent from an ethylene oligomerization reactor/system. In addition to the oligomer product, the composition (e.g., a reaction zone effluent) can contain catalyst (activated or deactivated) and an organic reaction medium. The separating (or fractionating) of the composition containing the oligomer product can occur in one or more steps —usually, multiple steps—to form the first oligomer composition and the heavies stream.

It is important to note that the oligomer product in the second process is different from the oligomer product in the first process, and the resulting fractionated compositions also are different. In the first process, the oligomer product comprises from 15 to 80 mol % $C_6$ olefins, from 20 to 80 mol % $C_8$ olefins, and from 5 to 20 mol % $C_{10}$+ olefin, while the oligomer product in the second process comprises at least 85 mol % $C_6$ olefins and at least 5 mol % $C_8$+ olefins. In the first process, the oligomer product is separated into a first oligomer composition (predominantly $C_6$), a second oligomer composition (predominantly $C_8$ ), and a heavies stream comprising $C_{10}$+ olefins, whereas the oligomer product in the second process is separated into a first oligomer composition (predominantly $C_6$) and a heavies stream comprising C$_8$+ olefins. The composition containing the oligomer product from the second process often can result from a 1-hexene process, whereas the composition containing the oligomer product from the first process can result from a 1-hexene/1-octene process.

As it pertains to the second process, the oligomer product in step a) contains at least 85 mol % C$_6$ olefins and at least 5 mol % C$_8$+ olefins prior to separating (or fractionating). For instance, the oligomer product can contain at least 87 mol % C$_6$ olefins in one aspect, at least 90 mol % C$_6$ olefins in another aspect, at least 91 mol % C$_6$ olefins in yet another aspect, and at least 93 mol % C$_6$ olefins in still another aspect. Additionally or alternatively, the oligomer product can contain from 5 to 15 mol % C$_8$+ olefins; alternatively, from 5 to 12 mol % C$_8$+ olefins; alternatively, from 6 to 14 mol % C$_8$+ olefins; or alternatively, from 7 to 13 mol % C$_8$+ olefins. As one of skill in the art would readily recognize, the total of these and other components does not exceed 100 mol %.

The composition containing the oligomer product is separated into i) a first oligomer composition comprising C$_6$ alkanes and at least 90 mol % C$_6$ olefins, the C$_6$ olefins comprising at least 90 mol % 1-hexene, and ii) a heavies stream comprising C$_8$+ olefins. Referring now to the first oligomer composition which, in some aspects, can contain at least 92 mol %, at least 94 mol %, at least 96 mol %, or at least 98 mol % C$_6$ olefins. Therefore, typical ranges for the amount of C$_6$ olefins in the first oligomer composition can include, but are not limited to, from 92 to 99 mol %, from 94 to 99.9 mol %, from 96 to 99.9 mol %, from 98 to 99.9 mol %, and the like. At least 90 mol % of the C$_6$ olefins is 1-hexene, but more often, the C$_6$ olefins contain at least 94 mol %, at least 96 mol %, or at least 98 mol % 1-hexene; therefore, typical ranges include from 90 mol % to 99 mol %, from 94 mol % to 99.9 mol %, from 96 mol % to 99.9 mol %, or from 98 to 99.9 mol % 1-hexene. In addition to 1-hexene, the C$_6$ olefins can contain often minimal amounts of internal and cyclic C$_6$ olefins (e.g., 2-hexene, 3-hexene, methylenecyclopentane, etc.), and the C$_6$ olefins often can contain from 0.1 mol % to 3 mol %, from 0.2 mol % to 2 mol %, or from 0.25 mol % to 1 mol %, of a total of internal and cyclic C$_6$ olefins. C$_6$ alkanes also are present in the first oligomer composition at often minimal amounts; representative C$_6$ alkanes include methylcyclopentane and n-hexane. Generally, the first oligomer composition in the second process contains from 0.1 mol % to 1.5 mol %, from 0.15 mol % to 1 mol %, or from 0.2 mol % to 0.75 mol %, C$_6$ alkanes.

Step b), step c), and step d) of the second process can be performed generally as described herein for the respective step b), step c), and step d) of the first process.

Optionally, similar to the first process, the second process—prior to step c)—can further comprise a step of isolating a composition comprising at least 90 mol %, at least 93 mol %, or at least 96 mol % C$_{10}$ linear internal olefins from the first composition. Any suitable technique can be used, such as extraction, filtration, evaporation, distillation, and the like, as well as any combination thereof. Beneficially, C$_6$ alkanes in the first oligomer composition do not metathesize, so these materials will be relatively easy to separate from C$_{10}$ linear internal olefins. Likewise, methylenecyclopentane is unreactive in metathesis, so this material also will be relatively easy to separate from C$_{10}$ linear internal olefins. Further, internal C$_6$ olefins metathesize to form non-C$_{10}$ olefins, which also become easier to separate from C$_{10}$ linear internal olefins.

Metathesis Catalyst Systems

While not limited thereto, the metathesis catalyst systems disclosed herein can be used to convert 1-hexene in the first oligomer composition to form a first composition containing C$_{10}$ linear internal olefins. Any suitable metathesis catalyst system can be used in the metathesis step, non-limiting examples of which can include a metal oxide based metathesis catalyst system, a metal halide based metathesis catalyst system, a metal carbene based metathesis catalyst system, or any combination thereof. In one aspect, the metathesis catalyst system can be a metal oxide based metathesis catalyst system or a metal halide based metathesis catalyst system, while in another aspect, the metathesis system catalyst can be a metal oxide based metathesis catalyst system; alternatively, a metal halide based metathesis catalyst system; or alternatively, a metal carbene based metathesis catalyst system.

Metal oxide based metathesis catalyst systems can comprise (or consist essentially of, or consist of) cobalt oxide, molybdenum oxide, tungsten oxide, rhenium oxide, or any combination thereof. For instance, the metal oxide based catalyst system can comprise (or consist essentially of, or consist of) cobalt oxide; alternatively, molybdenum oxide; alternatively, tungsten oxide; or alternatively, rhenium oxide. Optionally, the metal oxide based metathesis catalyst system can further comprise a support, or a metal alkyl activator, or both a support and a metal alkyl activator. Illustrative supports can include alumina, silica, silica-alumina, and aluminum-phosphate, amongst other solid oxide materials. Accordingly, non-limiting examples of supported metal oxide based metathesis catalyst systems can include molybdenum oxide on alumina (MoO$_3$/Al$_2$O$_3$), tungsten oxide on silica (WO$_3$/SiO$_2$), rhenium oxide on alumina (Re$_2$O$_7$/Al$_2$O$_3$), cobalt oxide and molybdenum oxide on alumina (CoO/MoO$_3$/Al$_2$O$_3$), and rhenium oxide on alumina activated with tetramethyl tin (Re$_2$O$_7$/Al$_2$O$_3$/SnMe$_4$). Other suitable metal oxide based metathesis catalyst systems are known to those skilled in the art.

Further, the metal oxide based metathesis catalyst system can include a metal alkyl activator, which can include alkyl lithium, alkyl magnesium, alkyl aluminum, alkyl tin compounds, or any mixture thereof. In an aspect, the metal alkyl activator can be an alkyl lithium compound. In another aspect, the metal alkyl activator can be an alkyl magnesium compound. In another aspect, the metal alkyl activator can be an alkyl aluminum compound. In yet another aspect, the metal alkyl activator can be an alkyl tin compound. Non-limiting examples of alkyl aluminum compounds can include trialkyl aluminum compounds and/or alkyl aluminum halide compounds. The alkyl groups on the metal alkyl activator can include any C$_1$ to C$_{10}$ hydrocarbyl group, or alternatively, any C$_1$ to C$_5$ hydrocarbyl group. In various aspects, the alkyl group for the metal alkyl activator can be a methyl group, ethyl group, n-propyl group, iso-propyl group, n-butyl group, sec-butyl group, or tert-butyl group; alternatively, a methyl group, ethyl group, n-butyl group, sec-butyl group, or tert-butyl group; alternatively, a methyl group; alternatively, an ethyl group; alternatively, an n-butyl group; alternatively, a sec-butyl group; or alternatively, a tert-butyl group. Representative examples of suitable trialkyl aluminum compounds can include trimethylaluminum, triethylaluminum, and triisobutylaluminum. The halide of the alkyl aluminum halide compound can be chloride, bromide, or iodide; alternatively, chloride; alternatively, bromide; or alternatively, iodide. Examples of suitable alkyl aluminum halide compounds can include ethylaluminum dichloride, diethylaluminum chloride, and ethylaluminum sesquichloride. Suitable and non-limiting examples of alkyl tin compounds can include tetramethyl tin, tetraethyl tin, and tetrabutyl tin.

Metal halide based metathesis catalyst systems can comprise (or consist essentially of, or consist of) a halide of tungsten, a halide of molybdenum, or a combination thereof. For instance, the metal halide based metathesis catalyst system can comprise (or consist essentially of, or consist of) a halide of tungsten, or alternatively, a halide of molybdenum. The halide of the metal halide based metathesis catalyst system can be chloride, bromide, or iodide. In one aspect, the halide can be chloride, and in another aspect, the halide can be bromide, and in yet another aspect, the halide can be iodide. Hence, the metal halide based metathesis catalyst system can comprise (or consist essentially of, or consist of) tungsten chloride, molybdenum chloride, or a mixture thereof; alternatively, tungsten chloride; or alternatively, molybdenum chloride.

Optionally, the metal halide based metathesis catalyst system can further comprise a metal alkyl activator (as described herein), oxygen, an alcohol, or any combination thereof; alternatively, a metal alkyl activator; alternatively, oxygen; or alternatively, an alcohol. Non-limiting examples of metal halide based metathesis catalyst systems can include tungsten chloride/tetrabutyl tin ($WCl_6/SnMe_4$), tungsten chloride/ethylaluminum dichloride ($WCl_6/EtAlCl_2$), tungsten chloride/ethyl-aluminum dichloride/ethyl alcohol ($WCl_6/EtAlCl_2/EtOH$), molybdenum chloride/triethyl aluminum ($MoCl_5/AlEt_3$), and molybdenum chloride/triethyl aluminum/$O_2$ ($MoCl_5/AlEt_3/O_2$). Other suitable metal halide based metathesis catalyst systems are known to those skilled in the art.

Metal carbene based metathesis catalyst systems can comprise (or consist essentially of, or consist of) tungsten, tantalum, osmium, molybdenum, ruthenium, or any combination thereof. For instance, the metal carbene based metathesis catalyst system can comprise (or consist essentially of, or consist of) tungsten; alternatively, tantalum; alternatively, osmium; alternatively, molybdenum; or alternatively, ruthenium. These metal carbene based metathesis catalyst systems can contain compounds which have a stable metal-carbon double bond or can form a metal-carbon double bond in situ from a metal precursor having a stable metal-carbon single bond.

In an aspect, a ruthenium carbene based metathesis catalyst system can comprise a compound having the structure $L^1L^2X_2Ru{=}CHR^1$, wherein $L^1$ and $L^2$ can be an organic ligand, X can be a halide, and $R^1$ can be hydrogen or a hydrocarbyl group. Generally, the compound in the ruthenium carbene based metathesis catalyst system having the structure $L^1L^2X_2Ru{=}CHR^1$ can be described using any combination of $L^1$, $L^2$, X, or $R^1$ described herein.

Generally, $L^1$ and $L^2$ independently can be $R'_3P$, an imidazolinylidene group, or an imidazolidinylidene group. In some aspects, $L^1$ and $L^2$ can be $R'_3P$; alternatively, $L^1$ can be $R'_3P$ and $L^2$ can be an imidazolinylidene group or an imidazolidinylidene group; alternatively, $L^1$ can be $R'_3P$ and $L^2$ can be an imidazolinylidene group; alternatively, $L^1$ can be $R'_3P$ and $L^2$ can be an imidazolidinylidene group; alternatively, $L^1$ and $L^2$ can be imidazolinylidene groups; or alternatively, $L^1$ and $L^2$ can be imidazolidinylidene groups. In aspects of this invention, R' can be a hydrocarbyl group, where each R' of $R'_3P$ can be the same; alternatively, each R' of $R'_3P$ can be different; or alternatively, one R' of $R'_3P$ can be different from the other two R' groups. In some aspects, each R' of $R'_3P$ independently can be a $C_1$ to $C_{15}$ hydrocarbyl group; or alternatively, a $C_1$ to $C_{10}$ hydrocarbyl group. In other aspects, each hydrocarbyl R' of $R'_3P$ independently can be an alkyl group or an aromatic group; alternatively, an alkyl group; or alternatively, an aromatic group. In an aspect, each alkyl R' of $R'_3P$ independently can be a methyl group, ethyl group, n-propyl group, isopropyl group, tert-butyl group, neo-pentyl group, cyclopentyl group, or cyclohexyl group. In some aspects, one or more R' groups of $R'_3P$ can be a phenyl group, or alternatively, a substituted phenyl group. In an aspect, the substituents of any substituted phenyl group independently can be a $C_1$-$C_5$ organyl group, or alternatively, a $C_1$-$C_5$ hydrocarbyl group. In some aspects, $R'_3P$ can be a trialkyl phosphine or triphenyl phosphine; alternatively, a trialkyl phosphine; or alternatively, triphenyl phosphine. In an aspect, $R'_3P$ can be trimethyl phosphine, triethyl phosphine, triisopropyl phosphine, tri-tert-butyl phosphine, tri-neopentyl phosphine, tricyclopentyl phosphine, tricyclohexyl phosphine, or triphenyl phosphine; alternatively, triisopropyl phosphine, tri-tert-butyl phosphine, tri-neopentyl phosphine, tricyclopentyl phosphine, tricyclohexyl phosphine, or triphenyl phosphine; alternatively, tricyclopentyl phosphine, tricyclohexyl phosphine, or triphenyl phosphine; alternatively, tricyclopentyl phosphine or tricyclohexyl phosphine; alternatively, tricyclopentyl phosphine; alternatively, tricyclohexyl phosphine; or alternatively triphenyl phosphine.

In an aspect, the imidazolinylidene group or imidazolidinylidene group can be a $C_3$ to $C_{80}$ imidazolinylidene group or imidazolidinylidene group; alternatively, a $C_3$ to $C_{50}$ imidazolinylidene group or imidazolidinylidene group; or alternatively, a $C_5$ to $C_{40}$ imidazolinylidene group or imidazolidinylidene group. In some aspects, the imidazolinylidene group can be a 1,3-disubstituted imidazolinylidene group. In some aspects, the imidazolidinylidene group can be a 1,3-disubstituted imidazolidinylidene group. In an aspect, the 1,3-substituents of the 1,3-disubstituted imidazolinylidene group or 1,3-disubstituted imidazolidinylidene group independently can be any suitable hydrocarbyl group. In an aspect, the 1,3-substituents of the 1,3-disubstituted imidazolinylidene group or 1,3-disubstituted imidazolidinylidene group independently can be a $C_1$ to $C_{30}$ hydrocarbyl group. In some aspects, the 1,3-substituents of the 1,3-disubstituted imidazolinylidene group or 1,3-disubstituted imidazolidinylidene group independently can be a $C_6$ to $C_{20}$ aromatic group or a $C_1$ to $C_{10}$ alkyl group. In other aspects, the 1,3-substituents of the 1,3-disubstituted imidazolinylidene group or 1,3-disubstituted imidazolidinylidene group independently can be a $C_6$ to $C_{20}$ aromatic group, or alternatively, a $C_1$ to $C_{10}$ alkyl group. In an aspect, each aromatic group of the 1,3-disubstituted imidazolinylidene group or 1,3-disubstituted imidazolidinylidene group independently can be a substituted aromatic group. In some aspects, the substituted aromatic group of the 1,3-disubstituted imidazolinylidene group or 1,3-disubstituted imidazolidinylidene group can be a 2-disubstituted phenyl group, a 2,6-disubstituted phenyl group, or a 2,4,6-trisubstituted phenyl group; alternatively, a 2,6-disubstituted phenyl group; or alternatively, a 2,4,6-trisubstituted phenyl group. Suitable substituents for any substituted phenyl group within the 1,3-disubstituted imidazolinylidene group or 1,3-disubstituted imidazolidinylidene group can include any $C_1$ to $C_{10}$ hydrocarbyl group, or alternatively, any $C_1$ to $C_5$ hydrocarbyl group. In some aspects, each hydrocarbyl substituent independently can be a methyl group, ethyl group, n-propyl group, iso-propyl group, n-butyl group, sec-butyl group, or tert-butyl group; alternatively, a methyl group, ethyl group, n-butyl group, sec-butyl group, or tert-butyl group; alternatively, a methyl group; alternatively, an ethyl group, alternatively, an isopropyl group; or alternatively, a tert-butyl group. In some aspects, each substituted aromatic group of the 1,3-disubstituted imidazolinylidene group or 1,3-disubstituted imidazolidinylidene group independently can be a 2,6-diisopropylphenyl group or a 2,4,6-trimethyl-phenyl group; alternatively, a 2,6-diisopropylphenyl group; or alternatively, a 2,4,6-trimethylphenyl group.

In various aspects, each X of the compound having the structure $L^1L^2X_2Ru=CHR^1$ independently can be chloride, bromide, or iodide. In an aspect, X can be chloride. In another aspect, X can be bromide. In yet another aspect, X can be iodide. $R^1$ of the compound having the structure $L^1L^2X_2Ru=CHR^1$ can be hydrogen or a $C_1$ to $C_{20}$ hydrocarbyl group. In some aspects, $R^1$ can be a methyl group, an ethyl group, an isopropyl group, a tert-butyl group, a phenyl group, a 2-methyl-2-propene group, or a 2,2-diphenylethene group. In other aspects, $R^1$ can be a tert-butyl group, a phenyl group, a 2-methyl-2-propene group, or a 2,2-diphenylethene group; alternatively, hydrogen; alternatively, a tert-butyl group; alternatively, a phenyl group; alternatively, a tert-butyl group; alternatively, a phenyl group; alternatively, a 2-methyl-2-propene group; or alternatively, a 2,2-diphenylethene group.

In some non-limiting aspects, the ruthenium carbene based metathesis catalyst system can comprise dichloro (phenylmethylene) bis(tricyclohexyl phosphine) ruthenium, dichloro(3-methyl-2-butenylidene) bis(tricyclohexyl phosphine) ruthenium, dichloro(3-methyl-2-butenylidene) bis (tri-cyclopentyl phosphine) ruthenium, 1,3-bis-(2,4,6-trimethylphenyl)-2-(imidazolidinylidene)(phenyl-methylene) dichloro(tricyclohexyl phosphine) ruthenium, or 1,3-bis-(2,6-diisopropylphenyl)-2-(imidazolidinylidene) (phenylmethylene)dichloro(tricyclohexyl phosphine) ruthenium. In some aspects, the ruthenium carbene based metathesis catalyst system can comprise dichloro(phenylmethyl-ene) bis(tricyclohexyl phosphine) ruthenium; alternatively, dichloro(3-methyl-2-butenylidene) bis(tri-cyclohexyl phosphine) ruthenium; alternatively, 1,3-bis-(2,4,6-trimethylphenyl)-2-(imidazolidinyl-idene)(phenylmethylene)dichloro(tricyclohexyl phosphine) ruthenium; or alternatively, 1,3-bis-(2,6-diisopropylphenyl)-2-(imidazolidinylidene) (phenylmethylene)dichloro(tricyclohexyl phosphine) ruthenium.

In an aspect, a molybdenum carbene based metathesis catalyst system can comprise a compound having the structure $Mo(=CHR^2)(NAr)(OR^3)_2$, wherein $R^2$ is a hydrogen or hydrocarbyl group, Ar is a substituted aromatic ring, and $R^3$ is a hydrocarbyl group or a halogenated hydrocarbyl group. Generally, the compound in the molybdenum carbene based metathesis catalyst system having the structure $Mo(=CHR^2)(NAr)(OR^3)_2$ can be described using any combination of $R^2$, Ar, and $R^3$ described herein.

In some aspects, $R^2$ of the compound having the structure $Mo(=CHR^2)(NAr)(OR^3)_2$ can be hydrogen or a $C_1$ to $C_{20}$ hydrocarbyl group, or alternatively, a $C_1$ to $C_{20}$ hydrocarbyl group. In some aspects, $R^2$ can be a methyl group, an ethyl group, an isopropyl group, a tert-butyl group, a phenyl group, a 2-methyl-2-propene group, or a 2,2-diphenylethene group. In other aspects, $R^2$ can be a tert-butyl group, a phenyl group, a 2-methyl-2-propene group, or a 2,2-diphenylethene group; alternatively, a tert-butyl group or a phenyl group; alternatively, hydrogen; alternatively, a tert-butyl group; alternatively, a phenyl group; alternatively, a 2-methyl-2-propene group; or alternatively, a 2,2-diphenylethene group.

In an aspect, the substituted aromatic ring, Ar, of the compound having the structure $Mo(=CHR^2)(NAr)(OR^3)_2$ can be a $C_6$ to $C_{30}$ aromatic group, or alternatively, a $C_6$ to $C_{20}$ aromatic group. In some aspects, each substituent of the substituted aromatic ring, Ar, independently can be a $C_6$ to $C_{20}$ hydrocarbyl group, a $C_1$ to $C_{10}$ hydrocarbyl group, or a $C_1$ to $C_5$ hydrocarbyl group. In some aspects, the substituted aromatic ring, Ar, can be a 2-substituted phenyl group, a 2,6-disubstituted phenyl group, or a 2,4,6-trisubstituted phenyl group. In an aspect, each substituent of the substituted aromatic ring independently can be a methyl group, an ethyl group, an isopropyl group, a tert-butyl group, or a neopentyl group; alternatively, a methyl group, an isopropyl group, or a tert-butyl group; alternatively, a methyl group or an isopropyl group. In some aspects, each substituent of the substituted aromatic ring independently can be a methyl group; alternatively, an isopropyl group; or alternatively, a tert-butyl group. In some non-limiting aspects, the substituted aromatic ring, Ar, can be a 2-tert-butylphenyl group, a 2,6-dimethylphenyl group, a 2,6-diisopropylphenyl group, or a 2,4,6-trimethyl phenyl group; alternatively, a 2-tert-butylphenyl group; alternatively, a 2,6-dimethylphenyl group; alternatively, a 2,6-diisopropylphenyl group; or alternatively, a 2,4,6-trimethyl phenyl group.

In an aspect, each $R^3$ of the compound having the structure $Mo(=CHR^2)(NAr)(OR^3)_2$ independently can be a $C_1$ to $C_{10}$ organic group, or alternatively, a $C_1$ to $C_5$ organic group. In some aspects, the $C_1$ to $C_{10}$ or $C_1$ to $C_5$ organic group can be a hydrocarbylhalyl group (a group consisting of hydrogen, carbon, and halogen atoms); alternatively, a hydrocarbylfluoryl group (a group consisting of hydrogen, carbon, and fluorine atoms); or alternatively, a hydrocarbyl group. In an aspect, the halogen atoms of the hydrocarbylhalyl group can be fluorine, chlorine, bromine, iodine, or any combination thereof; alternatively, fluorine; alternatively, chlorine; alternatively, bromine; or alternatively, iodine. In some aspects, each $R^3$ independently can be a tert-butyl group or a hexafluoro-tert-butyl group. In other aspects, $(OR^3)_2$ can represent a single organic group wherein the two $R^3$ groups attached to the oxygen atoms are connected via a bond between any divalent, trivalent, or tetravalent atom within the $R^3$ groups. In further aspects, $(OR^3)_2$ can represent a single organic group wherein the two $R^3$ groups attached to the oxygen atoms are connected via a carbon-carbon bond between any carbon atom of the two $R^3$ groups.

In an aspect, the molybdenum carbene based metathesis catalyst system can comprise $Mo(=CH—C(CH_3)_3)(N-2,6-$ diisopropylphenyl)(OC(CH_3)_3)$, $Mo(=CH—C(CH_3)_2 (C_6H_5))(N-2,6$-diiso-propylphenyl)(OC(CH_3)_3)$, $Mo(=CH—C(CH_3)_3)(N-2,6$-diisopropylphenyl)(OC(CH_3) (CF_3)_2)$, or $Mo(=CH—C(CH_3)_2(C_6H_5))(N-2,6$-diisopropylphenyl)(OC(CH_3)(CF_3)_2)$. In other aspects, the molybdenum carbene based metathesis catalyst system can comprise $Mo(=CH—C(CH_3)_3)(N-2,6$-diiso-propylphenyl)(OC (CH_3)_3)$; alternatively, $Mo(=CH—C(CH_3)_2(C_6H_5))(N-2,6$-diisopropylphenyl)-(OC(CH_3)_3)$; alternatively, $Mo(=CH—C(CH_3)_3)(N-2,6$-diisopropylphenyl)(OC(CH_3)(CF_3)_2)$; or alternatively, $Mo(=CH—C(CH_3)_2(C_6H_5))(N-2,6$-diisopropylphenyl)(OC(CH_3)(CF_3)_2)$.

Optionally, the metal carbene based metathesis catalyst system can further comprise a support. Illustrative supports can include alumina, silica, silica-alumina, and aluminum-phosphate, amongst other solid oxide materials. Additionally, the support can comprise a polymer, and the metal carbene metathesis catalyst compound can be tethered to the support via any of the ligands which do not contain the metal-carbon double bond.

Catalytic Isomerization Catalyst Systems

In step c), all or a portion of the $C_{10}$ linear internal olefins—such as 5-decene—are contacted with a catalytic isomerization catalyst system in the presence of photochemical irradiation to form a second composition comprising 1-decene. Any suitable catalytic isomerization catalyst system can be used, so long as it can efficiently chain-walk the double bond to the terminal position. In one aspect, the catalytic isomerization catalyst system can comprise a photocatalyst, a hydrogen atom transfer agent, a metal ion, and a proton donor. Referring first to the photocatalyst, the photocatalyst can comprise a transition metal complex, an organic dye (e.g., 3,6-di-tert-butyl-9-mesityl-10-phenylacridinium tetrafluoroborate), 1,2,3,5-Tetrakis(carbazol-9-yl)-4,6-dicyanobenzene, or a semiconductor (e.g., $TiO_2$). Illustrate examples of transition metal complexes include iridium-based photocatalysts (e.g., $[Ir(dF(CF_3)ppy)_2(5,5'-d(CF_3)bpy)]PF_6$), ruthenium-based photocatalysts, and the like. While not limited thereto, a suitable photocatalyst often can have a redox potential in a range from 0.7 V to 2.0 V, compared to Fc+/Fc in MeCN, and in some instances, the redox potential can range from 1.3 to 1.8 V.

The hydrogen atom transfer agent can be a Bronsted base, which can comprise an organic base in some aspects, while the Bronsted base in other aspects can comprise a pyridine base (e.g., 4,4'-di-tert-butyl-2,2'-dipyridine), or a pyridyl ligand of the metal ion (e.g., 4,4'-di-tert-butyl-2,2'-dipyridyl). Other illustrative and non-limiting examples of transfer agents can include cyctochrome p450, an iron poryphyrin, an iron cyclam, chromyl chloride, $MnO_4$, an iron zeolite, and the like, as well as any combination thereof.

The metal ion component of the catalytic isomerization catalyst system can comprise a chromium ion (e.g., a chromium(II) ion, a chromium(III) ion), and for instance, the metal ion can comprise a metal salt (e.g., a chromium(II) dihalide, a chromium(III) trihalide). The proton donor can comprise an alcohol (e.g., a primary alcohol, a secondary alcohol, an aliphatic alcohol, a primary aliphatic alcohol, a fluorinated alcohol), a carboxylic acid, or water, and the like, as well as combinations thereof. Accordingly, the proton donor often can comprise a $C_1$-$C_8$ primary aliphatic alcohol, examples of which include methanol, ethanol, n-propanol, isopropanol, and so forth.

The relative amounts of the photocatalyst, the hydrogen atom transfer agent, the metal ion, and the proton donor in the catalytic isomerization catalyst system are not particularly limited. However, the molar ratio of the Bronsted base (or other transfer agent) to the photocatalyst often ranges from 5:1 to 1:1 (e.g., 3:1), and additionally or alternatively, the molar ratio of the metal ion to the photocatalyst often ranges from 3:1 to 1:1 (e.g., 2:1), and additionally or alternatively, the molar ratio of the proton donor to the photocatalyst often ranges from 3:1 to 1:1 (e.g., 1:1).

The amount of the photocatalyst in the catalytic isomerization catalyst system relative to the amount of $C_{10}$ linear internal olefins is not particularly limited. For instance, the amount of the photocatalyst based on the $C_{10}$ linear internal olefins can range from 0.1 mol % to 10 mol % in one aspect, from 0.5 mol % to 8 mol % in another aspect, and from 1 mol % to 5 mol % in yet another aspect.

With this catalyst system, step c) optionally can contact the catalyst system and $C_{10}$ linear internal olefins in the presence of a solvent. While not limited thereto, organic solvents such as acetonitrile, dioxane, trifluorobenzene, and the like, as well as mixtures thereof, can be utilized. Step c) can be conducted any suitable temperature. In some non-limiting aspects, the temperature can be in a range from 0° C. to 100° C.; alternatively, from 0° C. to 60° C.; alternatively, from 0° C. to 40° C.; alternatively, from 15° C. to 75° C.; alternatively, from 15° C. to 50° C.; alternatively, from 15° C. to 40° C.; alternatively, from 20° C. to 40° C.; or alternatively, from 30° C. to 40° C. These temperature ranges also are meant to encompass circumstances where step c) is conducted at a series of different temperatures, instead of at a single fixed temperature, falling within the respective temperature ranges.

Likewise, step c) can use any suitable photochemical irradiation. The photochemical irradiation can comprise any suitable wavelength(s) of light, such as blue light (e.g., light from a source of blue light), and the photochemical irradiation can include wavelengths in the 450 to 495 nm range, such as at or around 456 nm.

In another aspect, the catalytic isomerization catalyst system can comprise a photocatalyst, a metal-containing co-catalyst, and an optional disulfide compound. In this aspect, the photocatalyst can comprise a decatungstate, such as sodium decatungstate or tetrabutylamine decatungstate, although not limited thereto. The metal-containing co-catalyst can comprise, for instance, a cobalt-based co-catalyst, an example of which is a cobaloxime—$Co(dmgH(dmgH_2)Br_2$. When present, any suitable disulfide can be utilized, and a representative example is 2,4,6-triisopropylbenzene disulfide.

The relative amounts of the photocatalyst, the metal-containing co-catalyst, and the disulfide compound (if present) are not particularly limited. However, the molar ratio of the photocatalyst to the co-catalyst often ranges from 5:1 to 1:5, from 3:1 to 1:3, from 2:1 to 1:2, or from 1.3:1 to 1:1.3, and the like.

With this catalyst system, step c) optionally can contact the catalyst system and $C_{10}$ linear internal olefins in the presence of a solvent. While not limited thereto, organic solvents such as acetonitrile, acetone, and the like, as well as mixtures thereof, can be utilized. Step c) can be conducted any suitable temperature with this catalyst system. In some non-limiting aspects, the temperature can be in a range from 0° C. to 100° C.; alternatively, from 0° C. to 60° C.; alternatively, from 0° C. to 40° C.; alternatively, from 15° C. to 75° C.; alternatively, from 15° C. to 50° C.; alternatively, from 15° C. to 40° C.; alternatively, from 20° C. to 40° C.; or alternatively, from 20° C. to 30° C. These temperature ranges also are meant to encompass circumstances where step c) is conducted at a series of different temperatures, instead of at a single fixed temperature, falling within the respective temperature ranges.

As above, step c) can use suitable photochemical irradiation with this catalyst system. The photochemical irradiation can comprise any suitable wavelength(s) of light, often in the 300 to 500 nm range or in the 350 to 450 nm range, such as at or around 390 nm.

Manufacturing Systems

A first (1-octene and 1-decene) manufacturing system provided herein can comprise 1) an ethylene oligomerization system configured to oligomerize ethylene in the presence of a catalyst system or catalyst system components to form a composition comprising an oligomer product, the oligomer product comprising from 15 to 80 mol % $C_6$ olefins, from 20 to 80 mol % $C_8$ olefins, and from 5 to 20 mol % $C_{10}+$ olefins, 2) a fractionation system configured to separate the composition comprising the oligomer product into i) a first oligomer composition comprising 1-hexene, ii) a second oligomer composition comprising 1-octene, and iii) a heavies stream comprising $C_{10}+$ olefins, 3) a metathesis system configured to contact a metathesis catalyst system with all or a portion of the first oligomer composition to form a first composition comprising $C_{10}$ linear internal olefins, 4) a catalytic isomerization system configured to contact all or a portion of the $C_{10}$ linear internal olefins with a catalytic isomerization catalyst system in the presence of photochemical irradiation to form a second composition comprising 1-decene, and 5) a purification system configured to isolate a third composition comprising at least 90 mol % 1-decene from the second composition.

A second (1-hexene and 1-decene) manufacturing system provided herein can comprise 1) an ethylene oligomerization system configured to oligomerize ethylene in the presence of a catalyst system or catalyst system components to form a composition comprising an oligomer product, the oligomer product comprising at least 85 mol % $C_6$ olefins and at least 5 mol % $C_8+$ olefins, 2) a fractionation system configured to separate the composition comprising the oligomer product into a first oligomer composition comprising 1-hexene and a heavies stream comprising $C_8+$ olefins, 3) a metathesis system configured to contact a metathesis catalyst system with all or a portion of the first oligomer composition to form a first composition comprising $C_{10}$ linear internal olefins, 4) a catalytic isomerization system configured to contact all or a portion of the $C_{10}$ linear internal olefins with a catalytic isomerization catalyst system in the presence of photochemical irradiation to form a second composition comprising 1-decene, and 5) a purification system configured to isolate a third composition comprising at least 90 mol % 1-decene from the second composition.

Generally, the features of the first manufacturing system and the second manufacturing system are the same as those described generally herein for the respective first process and second process. Thus, any features of the first process and the second process can be applied to the respective first manufacturing system and the second manufacturing system.

Optionally, the first manufacturing system (or the second manufacturing system) can further comprise a metathesis purification system configured to isolate a composition comprising $C_{10}$ linear internal olefins from the first composition prior to the catalytic isomerization system. This purification system can comprise, for instance, extraction, filtration, evaporation, distillation, and the like, as well as any combination thereof.

Referring now to FIG. 1, which illustrates a 1-octene/1-decene manufacturing system 100 consistent with an aspect of the present disclosure. The system 100 can include an ethylene oligomerization system 110, a fractionation system 120, a metathesis system 130, a catalytic isomerization system 150, and a purification system 160. In FIG. 1, an ethylene feed stream 105 enters the ethylene oligomerization system 110. Other feed streams to the ethylene oligomerization system 110, such as for catalyst system or catalyst system components, reaction medium (if used), and hydrogen (if used) are not specifically shown in FIG. 1. It is understood by a skilled artisan that there may be many different inputs to the ethylene oligomerization system, and this disclosure is not limited only to those options described in reference to FIG. 1 or otherwise disclosed herein. In the ethylene oligomerization system 110, the ethylene introduced via ethylene feed stream 105 is oligomerized in the presence of a catalyst system (or catalyst system components) to form a composition 115 comprising an oligomer product, which is discharged from the ethylene oligomerization system 110. Generally, the oligomer product contains from 15 to 80 mol % $C_6$ olefins, from 20 to 80 mol % $C_8$ olefins, and from 5 to 20 mol % $C_{10}+$ olefins.

This composition 115 comprising the oligomer product enters the fractionation system 120, which separates the composition 115 into a heavies stream 122 comprising $C_{10}+$ olefins (and optionally, spent catalyst), a second oligomer composition 124 comprising 1-octene, and a first oligomer composition 125 comprising 1-hexene. The first oligomer composition 125 comprising 1-hexene can be split into a 1-hexene product stream 126 and a 1-hexene feed stream 128. Thus, all or a portion of the first oligomer composition 125 can be fed to the metathesis system 130 and contacted with a suitable metathesis catalyst system to form a first composition 135 comprising $C_{10}$ linear internal olefins, which exits the metathesis system 130.

In FIG. 1, the composition 135 comprising $C_{10}$ linear internal olefins enters the catalytic isomerization system 150 and is contacted with a catalytic isomerization catalyst system in the presence of photochemical irradiation in the catalytic isomerization system 150 to form a second composition 155 comprising 1-decene. If desired, the system 100 of FIG. 1 can include the purification system 160. The second composition 155 comprising 1-decene exits the catalytic isomerization system 150 and enters the purification system 160, where a third composition 165 comprising at least 90 mol % 1-decene is produced and is discharged from the purification system 160.

Figure 2:
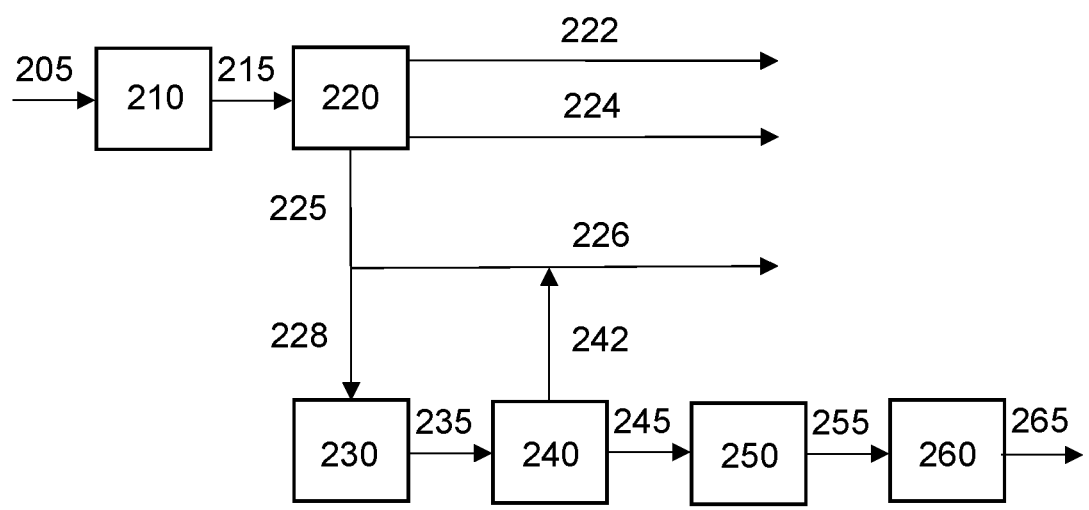
FIG. 2 illustrates a 1-octene/1-decene manufacturing system consistent with another aspect of the present disclosure.

Referring now to FIG. 2, which illustrates another 1-octene/1-decene manufacturing system 200 consistent with an aspect of the present disclosure. The system 200 can include an ethylene oligomerization system 210, a fractionation system 220, a metathesis system 230, a catalytic isomerization system 250, a purification system 260, an ethylene feed stream 205, a composition 215 comprising an oligomer product, a heavies stream 222 comprising $C_{10}+$ olefins (and optionally, spent catalyst), a second oligomer composition 224 comprising 1-octene, a first oligomer composition 225 comprising 1-hexene (which can be split into a 1-hexene product stream 226 and a 1-hexene feed stream 228), a second composition 255 comprising 1-decene, and a third composition 265 comprising at least 90 mol % 1-decene, which are generally the same as described for the similarly numbered components in FIG. 1.

In FIG. 2, the composition 235 comprising $C_{10}$ linear internal olefins exits the metathesis system 230 and enters a metathesis purification system 240 configured to isolate a composition 245 comprising $C_{10}$ linear internal olefins, which exits the metathesis purification system 240 and enters the catalytic isomerization system 250. A by-product stream 242 containing $C_6$ olefins is discharged from the metathesis purification system 240 and is combined with the 1-hexene product stream 226.

Figure 3:
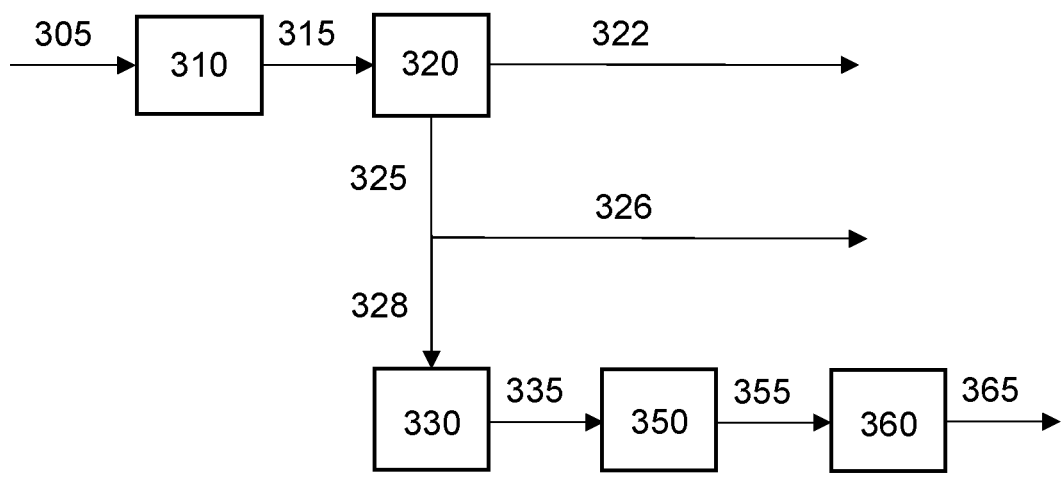
FIG. 3 illustrates a 1-hexene/1-decene manufacturing system consistent with yet another aspect of the present disclosure.

Referring now to FIG. 3, which illustrates a 1-hexene/1-decene manufacturing system 300 consistent with an aspect of the present disclosure. The system 300 can include a metathesis system 330, a catalytic isomerization system 350, a purification system 360, an ethylene feed stream 305, a first composition 335 comprising $C_{10}$ linear internal olefins, a second composition 355 comprising 1-decene, and a third composition 365 comprising at least 90 mol % 1-decene, which are generally the same as described for the similarly numbered components in FIG. 1.

In FIG. 3, the ethylene feed stream 305 enters an ethylene oligomerization system 310. Other feed streams to the ethylene oligomerization system 310, such as for catalyst system or catalyst system components, reaction medium (if used), and hydrogen (if used) are not specifically shown in FIG. 3. It is understood by a skilled artisan that there may be many different inputs to the ethylene oligomerization system, and this disclosure is not limited only to those options described in reference to FIG. 3 or otherwise disclosed herein. In the ethylene oligomerization system 310, the ethylene introduced via ethylene feed stream 305 is oligomerized in the presence of a catalyst system (or catalyst system components) to form a composition 315 comprising an oligomer product, which is discharged from the ethylene oligomerization system 310. Generally, and unlike FIGS. 1-2, the oligomer product in FIG. 3 contains at least 85 mol % $C_6$ olefins and at least 5 mol % $C_8$+ olefins (selective 1-hexene production).

This composition 315 comprising the oligomer product enters a fractionation system 320, which separates the composition 315 into a heavies stream 322 comprising $C_8$+ olefins (and optionally, spent catalyst) and a first oligomer composition 325 comprising 1-hexene. The first oligomer composition 325 comprising 1-hexene can be split into a 1-hexene product stream 326 and a 1-hexene feed stream 328. Thus, all or a portion of the first oligomer composition 325 can be fed to the metathesis system 330 and contacted with a suitable metathesis catalyst system to form a first composition 335 comprising $C_{10}$ linear internal olefins, which exits the metathesis system 330.

Normal Alpha Olefin Synthesis

Aspects of this invention also are directed to processes for producing normal alpha olefins. For instance, a third process described herein can comprise (or consist essentially of, or consist of) (i) contacting a first normal alpha olefin having the structure $CH_3(CH_2)_nHC=CH_2$ and a metathesis catalyst system to form a linear internal olefin having the structure $CH_3(CH_2)_nHC=CH(CH_2)_nCH_3$, and (ii) contacting the linear internal olefin with a catalytic isomerization catalyst system in the presence of photochemical irradiation to form a second normal alpha olefin having the structure $CH_3(CH_2)_{2n+1}HC=CH_2$. In the third process, n is an integer that can range from 0 to 15. Generally, the features of this process (e.g., the first normal alpha olefin, the metathesis catalyst, the linear internal olefin, the catalytic isomerization catalyst system, the second normal olefin, and the conditions under which each of the steps are conducted, among other features) are independently described herein and these features can be combined in any combination to further describe the disclosed normal alpha olefin synthesis processes. Moreover, additional process steps can be performed before, during, and/or after any of the steps of any of the processes disclosed herein, unless stated otherwise.

As described herein, n can be an integer that can range from 0 to 15. In one aspect consistent with this invention, n can be an integer from 0 to 10, while in another aspect, n can be an integer from 0 to 7. Yet, in another aspect, n can be an integer from 1 to 7, and in still another aspect, n can be an integer from 1 to 5. For example, n can be equal to 1, equal to 2, equal to 3, equal to 4, and so forth.

In some aspects of this invention, the first normal alpha olefin can comprise, consist essentially of, or consist of, propylene, 1-butene, 1-pentene, 1-hexene, 1-heptene, 1-octene, 1-nonene, 1-decene, 1-dodecene, 1-tetradecene, 1-hexadecene, 1-octadecene, or any combination thereof; alternatively, 1-butene, 1-pentene, 1-hexene, 1-heptene, 1-octene, or any combination thereof; or alternatively, 1-butene, 1-pentene, 1-hexene, or any combination thereof. In other aspects, the first normal alpha olefin can comprise, consist essentially of, or consist of, propylene; alternatively, 1-butene; alternatively, 1-pentene; alternatively, 1-hexene; alternatively, 1-heptene; alternatively, 1-octene; alternatively, 1-nonene; alternatively, 1-decene; alternatively, 1-dodecene; alternatively, 1-tetradecene; alternatively, 1-hexadecene; or alternatively, 1-octadecene.

In one aspect of this invention, the first normal alpha olefin can comprise (or consist essentially of, or consist of) 1-butene, and the second normal alpha olefin can comprise (or consist essentially of, or consist of) 1-hexene. In another aspect of this invention, the first normal alpha olefin can comprise (or consist essentially of, or consist of) 1-pentene, and the second normal alpha olefin can comprise (or consist essentially of, or consist of) 1-octene. In yet another aspect of this invention, the first normal alpha olefin can comprise (or consist essentially of, or consist of) 1-hexene, and the second normal alpha olefin can comprise (or consist essentially of, or consist of) 1-decene. In still another aspect of this invention, the first normal alpha olefin can comprise (or consist essentially of, or consist of) 1-octene, and the second normal alpha olefin can comprise (or consist essentially of, or consist of) 1-tetradecene.

The integer n, the first normal alpha olefin, and the second normal alpha olefin are described herein and their features can be utilized without limitation to further describe the normal alpha olefin synthesis processes disclosed herein. Other suitable values for the integer n and selections for the first normal alpha olefin and the second normal alpha olefin are readily apparent from this disclosure.

Step (i) of the third process often is referred to as the metathesis step, and in this step, the first normal alpha olefin having the structure $CH_3(CH_2)_nHC=CH_2$ is contacted with a metathesis catalyst system to form a linear internal olefin having the structure $CH_3(CH_2)_nHC=CH(CH_2)_nCH_3$. Any suitable metathesis catalyst system or any metathesis catalyst system disclosed herein can be used in the metathesis step of the third process, such as described herein in relation to the first process and the second process.

Step (ii) of the third process often is referred to as the catalytic isomerization step, and in this step, the linear internal olefin is contacted with a catalytic isomerization catalyst system in the presence of photochemical irradiation to form a second normal alpha olefin having the structure $CH_3(CH_2)_{2n+1}HC=CH_2$. Any suitable catalytic isomerization catalyst system or any catalytic isomerization catalyst system disclosed herein can be used in the catalytic isomerization step of the third process, such as described herein in relation to the first process and the second process.

Moreover, the features of step (i) and step (ii) of the third process can be any of those described herein for the respective metathesis and catalytic isomerization steps of the first process and second process. Thus, any features of the first process and the second process can be applied to the third process.

A fourth process is provided herein, and this process also is directed to producing normal alpha olefins. The fourth process can comprise (or consist essentially of, or consist of) (a) contacting a first normal alpha olefin having the structure $CH_3(CH_2)_pHC=CH_2$ and a second normal alpha olefin having the structure $CH_3(CH_2)_qHC=CH_2$ and a metathesis catalyst system to form a linear internal olefin having the structure $CH_3(CH_2)_pHC=CH(CH_2)_qCH_3$, and (b) contacting the linear internal olefin with a catalytic isomerization catalyst system in the presence of photochemical irradiation to form a third normal alpha olefin having the structure $CH_3(CH_2)_{p+q+1}HC=CH_2$. In the fourth process, p and q independently are integers in a range from 0 to 15. Generally, the features of this process (e.g., the first normal alpha olefin, the second normal alpha olefin, the metathesis catalyst, the linear internal olefin, the catalytic isomerization catalyst system, the third normal olefin, and the conditions under which each of the steps are conducted, among other features) are independently described herein and these features can be combined in any combination to further describe the disclosed normal alpha olefin synthesis processes. Moreover, additional process steps can be performed before, during, and/or after any of the steps of any of the processes disclosed herein, unless stated otherwise.

In this normal alpha olefin synthesis process, p and q independently can be integers that range from 0 to 15. In one aspect consistent with this invention, p and q independently can be an integer from 0 to 10, while in another aspect, p and q independently can be an integer from 1 to 10. Yet, in another aspect, p and q independently can be an integer from 1 to 7, and in still another aspect, p and q independently can be an integer from 1 to 5. For example, p and q independently can be equal to 1, equal to 2, equal to 3, or equal to 4. While not required, generally p and q are different integers.

The third normal alpha olefin produced in this process, having the structure $CH_3(CH_2)_{p+q+1}HC=CH_2$, is not particularly limited. However, in one aspect of this invention, the third normal alpha olefin can comprise, consist essentially of, or consist of, 1-butene, 1-hexene, 1-octene, 1-decene, 1-dodecene, 1-tetradecene, 1-hexadecene, 1-octadecene, or any combination thereof; alternatively, 1-hexene, 1-octene, 1-decene, 1-dodecene, 1-tetradecene, or any combination thereof; or alternatively, 1-hexene, 1-octene, 1-decene, or any combination thereof. In another aspect, the third normal alpha olefin can comprise, consist essentially of, or consist of, 1-butene; alternatively, 1-hexene; alternatively, 1-octene; alternatively, 1-decene; alternatively, 1-dodecene; alternatively, 1-tetradecene; alternatively, 1-hexadecene; or alternatively, 1-octadecene. In yet another aspect, the third normal alpha olefin can comprise, consist essentially of, or consist of, 1-hexene, 1-octene, 1-decene, or any combination thereof.

In one aspect of this invention, the first normal alpha olefin can comprise 1-butene, the second normal alpha olefin can comprise 1-octene, and the third normal alpha olefin can comprise 1-decene. In another aspect of this invention, the first normal alpha olefin can comprise 1-butene, the second normal alpha olefin can comprise 1-hexene, and the third normal alpha olefin can comprise 1-octene. In yet another aspect of this invention, the first normal alpha olefin can comprise propylene, the second normal alpha olefin can comprise pentene, and the third normal alpha olefin can comprise 1-hexene.

The integers p and q, the first normal alpha olefin, the second normal alpha olefin, and the third normal alpha olefin are described herein and their features can be utilized without limitation to further describe the normal alpha olefin synthesis processes disclosed herein. Other suitable values for the integers p and q and selections for the first normal alpha olefin, the second normal alpha olefin, and the third normal alpha olefin are readily apparent from this disclosure.

Step (a) and step (b) of the fourth process also can have any of the features and attributes (e.g., catalyst system, reaction conditions, etc.) as that described herein for step (i) and step (ii), respectively, of the third process, as well as any features or attributes described in the analogous steps of the first process and the second process.

EXAMPLES

The invention is further illustrated by the following examples, which are not to be construed in any way as imposing limitations to the scope of this invention. Various other aspects, modifications, and equivalents thereof which, after reading the description herein, can suggest themselves to one of ordinary skill in the art without departing from the spirit of the present invention or the scope of the appended claims.

Constructive Example A

Constructive Example A demonstrates the conversion of 1-hexene to 1-decene via a metathesis (homogeneous) and contra-isomerization pathway as shown in the synthesis scheme below (where n=3).

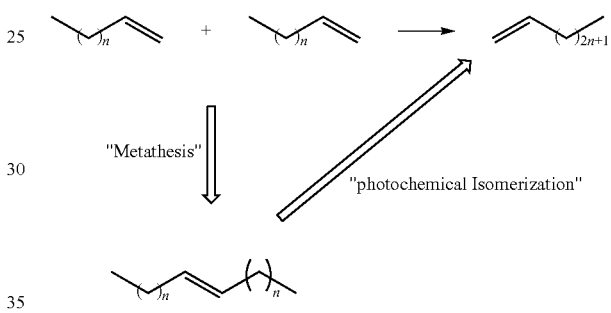

The reaction scheme for the homogeneous metathesis step is shown below.

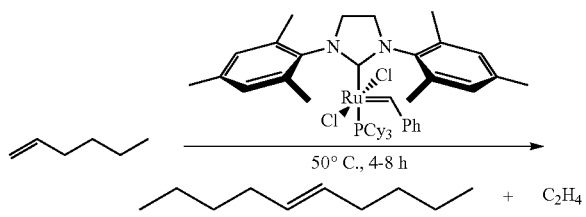

The metathesis step can be performed as follows. In a drybox under an $N_2$ atmosphere, a 500 mL round bottom flask with a magnetic stir bar is charged with 1-hexene (250 mL, 168 g, ~2 mol). The flask is placed in an aluminum block on a temperature controlled heating plate at ~50° C. and allowed to equilibrate temperature. To this stirring solution, a Grubbs $2^{nd}$ Generation Catalyst (dichloro [1,3-bis(2,4,6-trimethylphenyl)-2-imidazolidinylidene] (benzylidene) (tricyclohexyl-phosphine) ruthenium(II), 4.2 mg, 4.9 μmol is added to initiate the reaction. Reaction progress can be monitored by taking aliquot samples and analyzing them by GC-FID for reaction equilibrium, which typically takes 4-8 hr. Any produced ethylene is allowed to bubble and leave the flask as it is not capped in the glovebox. Upon completion of the reaction, the solution is cooled, filtered, and the reaction contents distilled to isolate 5-decene. The reaction yield is ~40-50% 5-decene by fractional distillation.

The reaction scheme for the photochemical induced isomerization step is shown below.

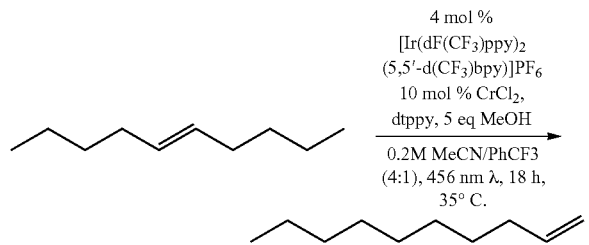

The contra-isomerization step can be performed as follows. A continuously stirred autoclave is charged with 1 mol of 5-decene under nitrogen. To this vessel, Ir(dF(CF$_3$)ppy)$_2$(5,5'-d(CF$_3$)bpy)]PF$_6$ (40 mmol, 4.0 mol %), 4,4'-di-tert-butyl-2,2'-dipyridyl (150 mmol, 15.0 mol %), and CrCl$_2$ (100 mmol, 10 mol %) are added. Then, a solution of PhCF$_3$ (6 L), MeCN (24 L), and MeOH (12 L) is charged via an addition port. The autoclave contains a light cell for irradiation at ~450 nm for 18 hr. The autoclave can have a temperature control cooling jacket attached to a process cooler that maintains the reaction temperature at 35° C. After completion of the reaction, the light source is shut off and the reactor is discharged through a filter plug of silica to remove any residual solids and polar compounds. Analysis of the mixture by GC-FID reveals >90 mol % conversion to 1-decene. The material can be purified by fractional distillation using a BR Instruments auto-distillation system monitoring for an atmospheric distillation temperature of 172° C.

Constructive Example B

Constructive Example B is similar to Constructive Example A, except that a different contra-isomerization pathway is used. The reaction scheme for the photochemical induced isomerization step is shown below.

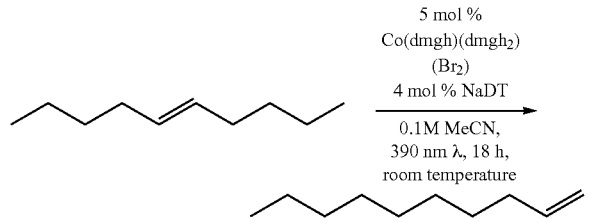

The contra-isomerization step can be performed as follows. A continuously stirred autoclave is charged with 1 mol of 5-decene under nitrogen. To this vessel, Co(dmgh)(dmgH$_2$)(Br$_2$) (50 mmol, 5.0 mol %), and decatungstate catalyst (40 mmol, 4.0 mol %) are added. Then, a solution of MeCN (10 L) is charged via an addition port. The autoclave contains a light cell for irradiation at ~390 nm for 18 hr. The autoclave can have a temperature control cooling jacket attached to a process cooler that maintains the reaction temperature at room temperature (18-22° C.). After completion of the reaction, the light source is shut off and the reactor is discharged through a filter plug of silica to remove any residual solids and polar compounds. Analysis of the mixture by GC-FID reveals >90 mol % conversion to 1-decene. The material can be purified by fractional distillation using a BR Instruments auto-distillation system monitoring for an atmospheric distillation temperature of 172° C.

The invention is described herein with reference to numerous aspects and specific examples. Many variations will suggest themselves to those skilled in the art in light of the detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A process (e.g., to make 1-octene/1-decene) comprising: a) separating a composition comprising an oligomer product, the oligomer product comprising from 15 to 80 mol % C$_6$ olefins, from 20 to 80 mol % C$_8$ olefins, and from 5 to 20 mol % C$_{10}$+ olefins, into i) a first oligomer composition comprising C$_6$ alkanes and at least 85 mol % C$_6$ olefins, the C$_6$ olefins comprising at least 80 mol % 1-hexene, ii) a second oligomer composition comprising at least 20 mol % C$_8$ olefins, the C$_8$ olefins comprising at least 85 mol % 1-octene, and iii) a heavies stream comprising C$_{10}$+ olefins; b) contacting a metathesis catalyst system with all or a portion of the first oligomer composition to form a first composition comprising C$_{10}$ linear internal olefins; c) contacting all or a portion of the C$_{10}$ linear internal olefins with a catalytic isomerization catalyst system in the presence of photochemical irradiation to form a second composition comprising 1-decene; and d) purifying the second composition to isolate a third composition comprising at least 90 mol % 1-decene.

Aspect 2. The process defined in aspect 1, wherein the oligomer product comprises from 30 to 70 mol % or from 35 to 65 mol % C$_6$ olefins (or any other minimum value, maximum value, or range described herein).

Aspect 3. The process defined in aspect 1 or 2, wherein the oligomer product comprises from 30 to 70 mol % or from 35 to 65 mol % C$_8$ olefins (or any other minimum value, maximum value, or range described herein).

Aspect 4. The process defined in any one of aspects 1-3, wherein the oligomer product comprises from 5 to 18 mol % or from 7 to 20 mol % C$_{10}$+ olefins (or any other minimum value, maximum value, or range described herein).

Aspect 5. The process defined in any one of aspects 1-4, wherein the first oligomer composition comprises at least 90 mol %, at least 93 mol %, or at least 95 mol % C$_6$ olefins (or any other minimum value, maximum value, or range described herein).

Aspect 6. The process defined in any one of aspects 1-5, wherein the first oligomer composition comprises from 0.5 to 12 mol %, from 1 to 10 mol %, from 1.5 to 8 mol %, or from 2 to 6 mol % C$_6$ alkanes (or any other minimum value, maximum value, or range described herein).

Aspect 7. The process defined in any one of aspects 1-6, wherein the C$_6$ olefins comprises at least 85 mol %, at least 90 mol %, at least 95 mol %, from 80 mol % to 98 mol %, from 80 mol % to 95 mol %, or from 85 mol % to 95 mol % 1-hexene (or any other minimum value, maximum value, or range described herein).

Aspect 8. The process defined in any one of aspects 1-7, wherein the C$_6$ olefins comprise from 0.1 to 10 mol %, from 0.5 to 8 mol %, or from 1 to 6 mol % internal and cyclic C$_6$ olefins (or any other minimum value, maximum value, or range described herein).

Aspect 9. The process defined in any one of aspects 1-8, wherein the second oligomer composition comprises at least 50 mol %, at least 75 mol %, at least 90 mol %, at least 95 mol %, at least 96 mol %, or at least 97 mol % $C_8$ olefins (or any other minimum value, maximum value, or range described herein).

Aspect 10. The process defined in any one of aspects 1-9, wherein the $C_8$ olefins comprise at least 90 mol %, at least 95 mol %, or at least 97 mol % 1-octene (or any other minimum value, maximum value, or range described herein).

Aspect 11. The process defined in any one of aspects 1-10, further comprising a step of isolating a composition comprising at least 90 mol %, at least 93 mol %, or at least 96 mol % $C_{10}$ linear internal olefins from the first composition prior to step c) via any suitable technique or any technique disclosed herein, e.g., extraction, filtration, evaporation, distillation, or any combination thereof.

Aspect 12. The process defined in any one of aspects 1-11, further comprising a step of contacting the metathesis catalyst system with all or a portion of the second oligomer composition comprising $C_8$ olefins to form a $C_{14}$ olefin composition.

Aspect 13. The process defined in any one of aspects 1-12, further comprising a step of contacting the metathesis catalyst with a light oligomer composition comprising $C_6$ and $C_8$ olefins to form a composition comprising $C_{10}$-$C_{14}$ linear internal olefins.

Aspect 14. A process (e.g., to make 1-hexene/1-decene) comprising: a) separating a composition comprising an oligomer product, the oligomer product comprising at least 85 mol % $C_6$ olefins and at least 5 mol % $C_8$+ olefins, into i) a first oligomer composition comprising $C_6$ alkanes and at least 90 mol % $C_6$ olefins, the $C_6$ olefins comprising at least 90 mol % 1-hexene, and ii) a heavies stream comprising $C_8$+ olefins; b) contacting a metathesis catalyst system with all or a portion of the first oligomer composition to form a first composition comprising $C_{10}$ linear internal olefins; c) contacting all or a portion of the $C_{10}$ linear internal olefins with a catalytic isomerization catalyst system in the presence of photochemical irradiation to form a second composition comprising 1-decene; and d) purifying the second composition to isolate a third composition comprising at least 90 mol % 1-decene.

Aspect 15. The process defined in aspect 14, wherein the oligomer product comprises at least 85 mol %, at least 87 mol %, at least 90 mol %, at least 91 mol %, or at least 93 mol % $C_6$ olefins (or any other minimum value, maximum value, or range described herein).

Aspect 16. The process defined in aspect 14 or 15, wherein the oligomer product comprises from 5 to 15 mol % or from 5 to 12 mol % $C_8$+ olefins (or any other minimum value, maximum value, or range described herein).

Aspect 17. The process defined in any one of aspects 14-16, wherein the first oligomer composition comprises at least 94 mol %, at least 96 mol %, or at least 98 mol % $C_6$ olefins (or any other minimum value, maximum value, or range described herein).

Aspect 18. The process defined in any one of aspects 14-17, wherein the first oligomer composition comprises from 0.1 mol % to 1.5 mol %, from 0.15 mol % to 1 mol %, or from 0.2 mol % to 0.75 mol % $C_6$ alkanes (or any other minimum value, maximum value, or range described herein).

Aspect 19. The process defined in any one of aspects 14-18, wherein the $C_6$ olefins comprise at least 94 mol %, at least 96 mol %, or at least 98 mol % 1-hexene (or any other minimum value, maximum value, or range described herein).

Aspect 20. The process defined in any one of aspects 14-19, wherein the $C_6$ olefins comprise from 0.1 mol % to 3 mol %, from 0.2 mol % to 2 mol %, or from 0.25 mol % to 1 mol % internal and cyclic $C_6$ olefins (or any other minimum value, maximum value, or range described herein).

Aspect 21. The process defined in any one of aspects 14-20, further comprising a step of isolating a composition comprising at least 90 mol %, at least 93 mol %, or at least 96 mol % $C_{10}$ linear internal olefins from the first composition prior to step c) via any suitable technique or any technique disclosed herein, e.g., extraction, filtration, evaporation, distillation, or any combination thereof.

Aspect 22. The process defined in any one of aspects 1-21, wherein the third composition comprises at least 95 mol % or at least 98 mol % 1-decene (or any other minimum value, maximum value, or range described herein).

Aspect 23. The process defined in any one of aspects 1-22, wherein purifying in step d) comprises any suitable technique or any technique disclosed herein, e.g., extraction, filtration, evaporation, distillation, or any combination thereof.

Aspect 24. The process defined in any one of aspects 1-23, wherein the metathesis catalyst system is a metal oxide based metathesis catalyst system, a metal halide based metathesis catalyst system, a metal carbene based metathesis catalyst system, or any combination thereof.

Aspect 25. The process defined in aspect 24, wherein the metal oxide based metathesis catalyst system comprises cobalt oxide, molybdenum oxide, tungsten oxide, rhenium oxide, or any combination thereof.

Aspect 26. The process defined in aspect 25, wherein the metal oxide based metathesis catalyst system further comprises a support and/or a metal alkyl activator.

Aspect 27. The process defined in aspect 24, wherein the metal halide based metathesis catalyst system comprises a halide of tungsten, a halide of molybdenum, or any combination thereof.

Aspect 28. The process defined in aspect 27, wherein the metal halide based metathesis catalyst system further comprises a metal alkyl activator and/or oxygen or an alcohol.

Aspect 29. The process defined in aspect 24, wherein the metal carbene based metathesis catalyst system comprises tungsten, tantalum, osmium, molybdenum, ruthenium, or any combination thereof.

Aspect 30. The process defined in aspect 29, wherein the metal carbene based metathesis catalyst system further comprises a support.

Aspect 31. The process defined in any one of aspects 1-30, wherein the catalytic isomerization catalyst system comprises a photocatalyst, a hydrogen atom transfer agent, a metal ion, and a proton donor.

Aspect 32. The process defined in aspect 31, wherein the photocatalyst comprises a transition metal complex, an organic dye (e.g., 3,6-di-tert-butyl-9-mesityl-10-phenylacridinium tetrafluoroborate), 1,2,3,5-Tetrakis(carbazol-9-yl)-4,6-dicyanobenzene, or a semiconductor (e.g., $TiO_2$).

Aspect 33. The process defined in aspect 32, wherein the transition metal complex comprises an iridium-based photocatalyst (e.g., $[Ir(dF(CF_3)ppy)_2(5,5'-d(CF_3)bpy)]PF_6$) or a ruthenium-based photocatalyst.

Aspect 34. The process defined in any one of aspects 31-33, wherein the photocatalyst has a redox potential in a range from 0.7 V to 2.0 V, compared to Fc+/Fc in MeCN, or from 1.3 to 1.8 V.

Aspect 35. The process defined in any one of aspects 31-34, wherein the transfer agent is a Bronsted base comprising an organic base.

Aspect 36. The process defined in any one of aspects 31-35, wherein the transfer agent is a Bronsted base comprising a pyridine base (e.g., 4,4'-di-tert-butyl-2,2'-dipyridine), or a pyridyl ligand of the metal ion (e.g., 4,4'-di-tert-butyl-2,2'-dipyridyl).

Aspect 37. The process defined in any one of aspects 31-34, wherein the transfer agent comprises cyctochrome p450, an iron poryphyrin, an iron cyclam, chromyl chloride, $MnO_4$, an iron zeolite, or any combination thereof.

Aspect 38. The process defined in any one of aspects 31-37, wherein the metal ion comprises a chromium ion (e.g., a chromium(II) ion, a chromium(III) ion) or the metal ion comprises a metal salt (e.g., a chromium(II) dihalide, a chromium(III) trihalide).

Aspect 39. The process defined in any one of aspects 31-38, wherein the proton donor comprises an alcohol (e.g., a primary alcohol, a secondary alcohol, an aliphatic alcohol, a primary aliphatic alcohol, a fluorinated alcohol), a carboxylic acid, or water.

Aspect 40. The process defined in any one of aspects 31-38, wherein the proton donor comprises a $C_1$-$C_8$ primary aliphatic alcohol (e.g., methanol, ethanol, n-propanol, isopropanol).

Aspect 41. The process defined in any one of aspects 31-40, wherein the catalyst system further comprises a solvent (e.g., an organic solvent such as acetonitrile, dioxane, trifluorobenzene, or mixtures thereof).

Aspect 42. The process defined in any one of aspects 31-41, wherein step c) is performed at a temperature in a range from 0 to 40° C. (e.g., ~35° C., or any other minimum temperature, maximum temperature, or temperature range disclosed herein).

Aspect 43. The process defined in any one of aspects 31-42, wherein a molar ratio of the Bronsted base to the photocatalyst is in a range from 5:1 to 1:1 (e.g., 3:1), and/or a molar ratio of the metal ion to the photocatalyst is in a range from 3:1 to 1:1 (e.g., 2:1), and/or a molar ratio of the proton donor to the photocatalyst is in a range from 3:1 to 1:1 (e.g., 1:1), as well any other minimum ratio, maximum ratio, or range of ratios disclosed herein.

Aspect 44. The process defined in any one of aspects 31-43, wherein an amount of the photocatalyst in the catalyst system based on the $C_{10}$ linear internal olefins is in a range from 0.1 mol % to 10 mol %, or from 1 mol % to 5 mol % (or any other minimum amount, maximum amount, or range of amounts disclosed herein).

Aspect 45. The process defined in any one of aspects 31-44, wherein the photochemical irradiation comprises any suitable wavelength(s) of light or any wavelength disclosed herein, e.g., blue light, such as from 450 to 495 nm, or at ~456 nm.

Aspect 46. The process defined in any one of aspects 1-30, wherein the catalytic isomerization catalyst system comprises a photocatalyst, a metal-containing co-catalyst, and an optional disulfide compound.

Aspect 47. The process defined in aspect 46, wherein the photocatalyst comprises a decatungstate (e.g., sodium decatungstate, tetrabutylamine decatungstate).

Aspect 48. The process defined in aspect 46 or 47, wherein the co-catalyst comprises a cobalt-based co-catalyst (e.g., a cobaloxime).

Aspect 49. The process defined in aspect 46 or 47, wherein the co-catalyst comprises a cobaloxime (e.g., $Co(dmgH(dmgH_2)Br_2)$).

Aspect 50. The process defined in any one of aspects 46-49, wherein the disulfide compound comprises 2,4,6-triisopropylbenzene disulfide.

Aspect 51. The process defined in any one of aspects 46-50, wherein the catalyst system further comprises a solvent (e.g., an organic solvent such as acetonitrile, acetone, or a mixture thereof).

Aspect 52. The process defined in any one of aspects 46-51, wherein step c) is performed at a temperature in a range from 0 to 40° C. (e.g., ~25° C., or any other minimum temperature, maximum temperature, or temperature range disclosed herein).

Aspect 53. The process defined in any one of aspects 46-52, wherein a molar ratio of the photocatalyst to the co-catalyst is in a range from 2:1 to 1:2 (or any other minimum ratio, maximum ratio, or range of ratios disclosed herein).

Aspect 54. The process defined in any one of aspects 46-53, wherein the photochemical irradiation comprises any suitable wavelength(s) of light or any wavelength disclosed herein, e.g., from 300 to 500 nm, from 350 to 450 nm, or ~390 nm.

Aspect 55. A (1-octene/1-decene) manufacturing system comprising: 1) an ethylene oligomerization system configured to oligomerize ethylene in the presence of a catalyst system or catalyst system components to form a composition comprising an oligomer product, the oligomer product comprising from 15 to 80 mol % $C_6$ olefins, from 20 to 80 mol % $C_8$ olefins, and from 5 to 20 mol % $C_{10}$+ olefins; 2) a fractionation system configured to separate the composition comprising the oligomer product into i) a first oligomer composition comprising 1-hexene, ii) a second oligomer composition comprising 1-octene, and iii) a heavies stream comprising $C_{10}$+ olefins; 3) a metathesis system configured to contact a metathesis catalyst system with all or a portion of the first oligomer composition to form a first composition comprising $C_{10}$ linear internal olefins; 4) a catalytic isomerization system configured to contact all or a portion of the $C_{10}$ linear internal olefins with a catalytic isomerization catalyst system in the presence of photochemical irradiation to form a second composition comprising 1-decene; and 5) a purification system configured to isolate a third composition comprising at least 90 mol % 1-decene from the second composition.

Aspect 56. A (1-hexene/1-decene) manufacturing system comprising: 1) an ethylene oligomerization system configured to oligomerize ethylene in the presence of a catalyst system or catalyst system components to form a composition comprising an oligomer product, the oligomer product comprising at least 85 mol % $C_6$ olefins and at least 5 mol % $C_8$+ olefins; 2) a fractionation system configured to separate the composition comprising the oligomer product into a first oligomer composition comprising 1-hexene and a heavies stream comprising $C_8$+ olefins; 3) a metathesis system configured to contact a metathesis catalyst system with all or a portion of the first oligomer composition to form a first composition comprising $C_{10}$ linear internal olefins; 4) a catalytic isomerization system configured to contact all or a portion of the $C_{10}$ linear internal olefins with a catalytic isomerization catalyst system in the presence of photochemical irradiation to form a second composition comprising 1-decene; and 5) a purification system configured to isolate a third composition comprising at least 90 mol % 1-decene from the second composition.

Aspect 57. The manufacturing system defined in aspect 55 or 56, further comprising a metathesis purification system configured to isolate a composition comprising $C_{10}$ linear internal olefins from the first composition prior to the catalytic isomerization system, wherein the purification system comprises extraction, filtration, evaporation, distillation, or any combination thereof.

Aspect 58. The manufacturing system defined in any one of aspects 55-57, wherein the catalyst system or catalyst system components comprise a heteroatomic ligand chromium compound complex and an alkylaluminum compound, or a heteroatomic ligand, a chromium compound, and an alkylaluminum compound.

Aspect 59. The manufacturing system defined in any one of aspects 55-58, wherein the metathesis catalyst system is defined in any one of aspects 24-30.

Aspect 60. The manufacturing system defined in any one of aspects 55-59, wherein the catalytic isomerization catalyst system is defined in any one of aspects 31-54.

Aspect 61. A process comprising: (i) contacting a first normal alpha olefin having the structure $CH_3(CH_2)_n HC=CH_2$ and a metathesis catalyst system to form a linear internal olefin having the structure $CH_3(CH_2)_n HC=CH(CH_2)_n CH_3$; and (ii) contacting the linear internal olefin with a catalytic isomerization catalyst system in the presence of photochemical irradiation to form a second normal alpha olefin having the structure $CH_3(CH_2)_{2n+1} HC=CH_2$; wherein n is an integer from 0 to 15.

Aspect 62. The process defined in aspect 61, wherein n is an integer from 1 to 10.

Aspect 63. The process defined in aspect 61, wherein n is an integer from 1 to 7.

Aspect 64. The process defined in aspect 61, wherein the first normal alpha olefin comprises propylene, 1-butene, 1-pentene, 1-hexene, 1-heptene, 1-octene, 1-nonene, 1-decene, 1-dodecene, 1-tetradecene, 1-hexadecene, 1-octadecene, or any combination thereof.

Aspect 65. The process defined in aspect 61, wherein the first normal alpha olefin comprises 1-butene, 1-pentene, 1-hexene, 1-heptene, 1-octene, or any combination thereof.

Aspect 66. The process defined in aspect 61, wherein the first normal alpha olefin comprises 1-butene, and the second normal alpha olefin comprises 1-hexene.

Aspect 67. The process defined in aspect 61, wherein the first normal alpha olefin comprises 1-pentene, and the second normal alpha olefin comprises 1-octene.

Aspect 68. The process defined in aspect 61, wherein the first normal alpha olefin comprises 1-hexene, and the second normal alpha olefin comprises 1-decene.

Aspect 69. The process defined in aspect 61, wherein the first normal alpha olefin comprises 1-octene, and the second normal alpha olefin comprises 1-tetradecene.

Aspect 70. A process comprising: (a) contacting a first normal alpha olefin having the structure $CH_3(CH_2)_p HC=CH_2$ and a second normal alpha olefin having the structure $CH_3(CH_2)_q HC=CH_2$ and a metathesis catalyst system to form a linear internal olefin having the structure $CH_3(CH_2)_p HC=CH(CH_2)_q CH_3$; and (b) contacting the linear internal olefin with a catalytic isomerization catalyst system in the presence of photochemical irradiation to form a third normal alpha olefin having the structure $CH_3(CH_2)_{p+q+1} HC=CH_2$; wherein p and q independently are an integer from 0 to 15.

Aspect 71. The process defined in aspect 70, wherein p and q independently are an integer from 1 to 10.

Aspect 72. The process defined in aspect 70, wherein p and q independently are an integer from 1 to 7.

Aspect 73. The process defined in aspect 70, wherein the third normal alpha olefin comprises 1-butene, 1-hexene, 1-octene, 1-decene, 1-dodecene, 1-tetradecene, 1-hexadecene, 1-octadecene, or any combination thereof.

Aspect 74. The process defined in aspect 70, wherein the first normal alpha olefin comprises 1-butene, the second normal alpha olefin comprises 1-octene, and the third normal alpha olefin comprises 1-decene.

Aspect 75. The process defined in aspect 70, wherein the first normal alpha olefin comprises 1-butene, the second normal alpha olefin comprises 1-hexene, and the third normal alpha olefin comprises 1-octene.

Aspect 76. The process defined in aspect 70, wherein the first normal alpha olefin comprises propylene, the second normal alpha olefin comprises pentene, and the third normal alpha olefin comprises 1-hexene.

Aspect 77. The process defined in any one of aspects 61-76, wherein the metathesis catalyst system is defined in any one of aspects 24-30.

Aspect 78. The process defined in any one of aspects 61-77, wherein the catalytic isomerization catalyst system is defined in any one of aspects 31-54.

What is claimed is:
1. A process comprising:
   a) separating a composition comprising an oligomer product, the oligomer product comprising from 15 to 80 mol % $C_6$ olefins, from 20 to 80 mol % $C_8$ olefins, and from 5 to 20 mol % $C_{10}+$ olefins, into
      i) a first oligomer composition comprising $C_6$ alkanes and at least 85 mol % $C_6$ olefins, the $C_6$ olefins comprising at least 80 mol % 1-hexene,
      ii) a second oligomer composition comprising at least 20 mol % $C_8$ olefins, the $C_8$ olefins comprising at least 85 mol % 1-octene, and
      iii) a heavies stream comprising $C_{10}+$ olefins;
   b) contacting a metathesis catalyst system with all or a portion of the first oligomer composition to form a first composition comprising $C_{10}$ linear internal olefins;
   c) contacting all or a portion of the $C_{10}$ linear internal olefins with a catalytic isomerization catalyst system in the presence of photochemical irradiation to form a second composition comprising 1-decene; and
   d) purifying the second composition to isolate a third composition comprising at least 90 mol % 1-decene.

2. The process of claim 1, wherein the oligomer product comprises from 35 to 65 mol % $C_6$ olefins, from 35 to 65 mol % $C_8$ olefins, and from 5 to 18 mol % $C_{10}+$ olefins.

3. The process of claim 1, wherein:
   the first oligomer composition comprises from 1.5 to 8 mol % $C_6$ alkanes and at least 90 mol % $C_6$ olefins; and
   the $C_6$ olefins comprises at least 90 mol % 1-hexene and from 0.5 to 8 mol % internal and cyclic $C_6$ olefins.

4. The process of claim 1, wherein:
   the second oligomer composition comprises at least 90 mol % $C_8$ olefins; and
   the $C_8$ olefins comprise at least 95 mol % 1-octene.

5. The process of claim 1, further comprising a step of isolating an internal olefin composition comprising at least 90 mol % $C_{10}$ linear internal olefins from the first composition prior to step c).

6. The process of claim 1, wherein the metathesis catalyst system is a metal oxide based metathesis catalyst system, a metal halide based metathesis catalyst system, a metal carbene based metathesis catalyst system, or any combination thereof.

7. The process of claim 1, wherein the catalytic isomerization catalyst system comprises a photocatalyst, a hydrogen atom transfer agent, a metal ion, and a proton donor.

8. The process of claim 1, wherein the catalytic isomerization catalyst system comprises a photocatalyst, a metal-containing co-catalyst, and an optional disulfide compound.

9. The process of claim 1, wherein the third composition comprises at least 95 mol % 1-decene.

10. A process comprising:
   a) separating a composition comprising an oligomer product, the oligomer product comprising at least 85 mol % $C_6$ olefins and at least 5 mol % $C_8$+ olefins, into
      i) a first oligomer composition comprising $C_6$ alkanes and at least 90 mol % $C_6$ olefins, the $C_6$ olefins comprising at least 90 mol % 1-hexene, and
      ii) a heavies stream comprising $C_8$+ olefins;
   b) contacting a metathesis catalyst system with all or a portion of the first oligomer composition to form a first composition comprising $C_{10}$ linear internal olefins;
   c) contacting all or a portion of the $C_{10}$ linear internal olefins with a catalytic isomerization catalyst system in the presence of photochemical irradiation to form a second composition comprising 1-decene; and
   d) purifying the second composition to isolate a third composition comprising at least 90 mol % 1-decene.

11. The process of claim 10, wherein the oligomer product comprises at least 90 mol % $C_6$ olefins.

12. The process of claim 10, wherein:
   the first oligomer composition comprises at least 94 mol % $C_6$ olefins; and
   the $C_6$ olefins comprises at least 96 mol % 1-hexene.

13. The process of claim 10, further comprising a step of isolating an internal olefin composition comprising at least 90 mol $C_{10}$ linear internal olefins from the first composition prior to step c).

14. A 1-octene/1-decene manufacturing system comprising:
   1) an ethylene oligomerization system configured to oligomerize ethylene in the presence of a catalyst system or catalyst system components to form a composition comprising an oligomer product, the oligomer product comprising from 15 to 80 mol % $C_6$ olefins, from 20 to 80 mol % $C_8$ olefins, and from 5 to 20 mol % $C_{10}$+ olefins;
   2) a fractionation system configured to separate the composition comprising the oligomer product into i) a first oligomer composition comprising 1-hexene, ii) a second oligomer composition comprising 1-octene, and iii) a heavies stream comprising $C_{10}$+ olefins;
   3) a metathesis system configured to contact a metathesis catalyst system with all or a portion of the first oligomer composition to form a first composition comprising $C_{10}$ linear internal olefins;
   4) a catalytic isomerization system configured to contact all or a portion of the $C_{10}$ linear internal olefins with a catalytic isomerization catalyst system in the presence of photochemical irradiation to form a second composition comprising 1-decene; and
   5) a purification system configured to isolate a third composition comprising at least 90 mol % 1-decene from the second composition.

15. The manufacturing system of claim 14, further comprising a metathesis purification system configured to isolate a composition comprising $C_{10}$ linear internal olefins from the first composition prior to the catalytic isomerization system.

16. The manufacturing system of claim 15, wherein the purification system comprises extraction, filtration, evaporation, distillation, or any combination thereof.

17. The manufacturing system of claim 14, wherein the catalyst system or catalyst system components comprise a heteroatomic ligand chromium compound complex and an alkylaluminum compound, or a heteroatomic ligand, a chromium compound, and an alkylaluminum compound.

18. A 1-hexene/1-decene manufacturing system comprising:
   1) an ethylene oligomerization system configured to oligomerize ethylene in the presence of a catalyst system or catalyst system components to form a composition comprising an oligomer product, the oligomer product comprising at least 85 mol % $C_6$ olefins and at least 5 mol % $C_8$+ olefins;
   2) a fractionation system configured to separate the composition comprising the oligomer product into a first oligomer composition comprising 1-hexene and a heavies stream comprising $C_8$+ olefins;
   3) a metathesis system configured to contact a metathesis catalyst system with all or a portion of the first oligomer composition to form a first composition comprising $C_{10}$ linear internal olefins;
   4) a catalytic isomerization system configured to contact all or a portion of the $C_{10}$ linear internal olefins with a catalytic isomerization catalyst system in the presence of photochemical irradiation to form a second composition comprising 1-decene; and
   5) a purification system configured to isolate a third composition comprising at least 90 mol % 1-decene from the second composition.

19. The manufacturing system of claim 18, further comprising a metathesis purification system configured to isolate a composition comprising $C_{10}$ linear internal olefins from the first composition prior to the catalytic isomerization system.

20. A process comprising:
   (i) contacting a first normal alpha olefin having the structure $CH_3(CH_2)_nHC=CH_2$ and a metathesis catalyst system to form a linear internal olefin having the structure $CH_3(CH_2)_nHC=CH(CH_2)_nCH_3$; and
   (ii) contacting the linear internal olefin with a catalytic isomerization catalyst system in the presence of photochemical irradiation to form a second normal alpha olefin having the structure $CH_3(CH_2)_{2n+1}HC=CH_2$;
   wherein n is an integer from 0 to 15;
   or
   (a) contacting a first normal alpha olefin having the structure $CH_3(CH_2)_pHC=CH_2$ and a second normal alpha olefin having the structure $CH_3(CH_2)_qHC=CH_2$ and a metathesis catalyst system to form a linear internal olefin having the structure $CH_3(CH_2)_pHC=CH(CH_2)_qCH_3$; and
   (b) contacting the linear internal olefin with a catalytic isomerization catalyst system in the presence of photochemical irradiation to form a third normal alpha olefin having the structure $CH_3(CH_2)_{p+q+1}HC=CH_2$;
   wherein p and q independently are an integer from 0 to 15.

21. The process of claim 20, wherein:
   the process comprises step (i) and step (ii); and
   the first normal alpha olefin comprises 1-butene, and the second normal alpha olefin comprises 1-hexene; or
   the first normal alpha olefin comprises 1-pentene, and the second normal alpha olefin comprises 1-octene; or
   the first normal alpha olefin comprises 1-hexene, and the second normal alpha olefin comprises 1-decene; or
   the first normal alpha olefin comprises 1-octene, and the second normal alpha olefin comprises 1-tetradecene.

22. The process of claim 20, wherein:

the process comprises step (a) and step (b); and the first normal alpha olefin comprises 1-butene, the second normal alpha olefin comprises 1-octene, and the third normal alpha olefin comprises 1-decene; or the first normal alpha olefin comprises 1-butene, the second normal alpha olefin comprises 1-hexene, and the third normal alpha olefin comprises 1-octene; or the first normal alpha olefin comprises propylene, the second normal alpha olefin comprises pentene, and the third normal alpha olefin comprises 1-hexene.

* * * * *